United States Patent
Wallace et al.

(10) Patent No.: US 11,950,769 B2
(45) Date of Patent: Apr. 9, 2024

(54) URINE COLLECTION, STORAGE, AND TESTING ASSEMBLY

(71) Applicants: David Wallace, Mesa, AZ (US); Sydney Wallace, Mesa, AZ (US); Joshua Chang, Tempe, AZ (US); Mark Naufel, Phoenix, AZ (US)

(72) Inventors: David Wallace, Mesa, AZ (US); Sydney Wallace, Mesa, AZ (US); Joshua Chang, Tempe, AZ (US); Mark Naufel, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 17/759,362

(22) PCT Filed: Jan. 29, 2021

(86) PCT No.: PCT/US2021/015741
§ 371 (c)(1),
(2) Date: Jul. 22, 2022

(87) PCT Pub. No.: WO2021/155174
PCT Pub. Date: Aug. 5, 2021

(65) Prior Publication Data
US 2023/0123656 A1   Apr. 20, 2023

Related U.S. Application Data

(60) Provisional application No. 62/968,758, filed on Jan. 31, 2020.

(51) Int. Cl.
*A61B 10/00* (2006.01)

(52) U.S. Cl.
CPC .................................. *A61B 10/007* (2013.01)

(58) Field of Classification Search
CPC ........................... A61B 10/007; A61B 10/0096
See application file for complete search history.

(56) References Cited

U.S. PATENT DOCUMENTS

| 228,031 A | 5/1880 | Broughton |
| 645,430 A | 3/1900 | Smelker |

(Continued)

FOREIGN PATENT DOCUMENTS

| CN | 206399701 U | 8/2017 |
| EP | 0483734 A1 | 5/1992 |

(Continued)

OTHER PUBLICATIONS

Adams JD, et al. The effect of storing temperature and duration on urinary hydration markers. Int J Sport Nutr Exerc Metab 2017; 27: 18-24.

(Continued)

*Primary Examiner* — Matthew Kremer
(74) *Attorney, Agent, or Firm* — Michael Best & Friedrich LLP

(57) ABSTRACT

A urine collection assembly includes a container; a funnel removably coupled to the container, the funnel in fluid communication with the container; a first collection chamber in selective communication with the funnel; a valve configured to allow selective communication between the first collection chamber and the funnel; a second collection chamber in selective communication with the funnel; and a lid removably coupleable to the funnel. A saddle may be removably coupleable to the funnel and configured to guide urine into the container.

11 Claims, 22 Drawing Sheets

(56) References Cited

U.S. PATENT DOCUMENTS

| | | | |
|---|---|---|---|
| 3,499,327 A | 3/1970 | Lane, Jr. | |
| 3,635,091 A | 1/1972 | Linzer et al. | |
| 3,722,503 A * | 3/1973 | Hovick | A61F 5/44 4/144.3 |
| 3,774,455 A | 11/1973 | Seidler et al. | |
| 3,832,738 A | 9/1974 | Kliemann | |
| 3,878,571 A | 4/1975 | Seeley | |
| 3,894,845 A | 7/1975 | McDonald | |
| 3,943,770 A | 3/1976 | Mcdonald | |
| 3,982,898 A | 9/1976 | Mcdonald | |
| 4,040,791 A | 8/1977 | Kuntz | |
| 4,064,760 A | 12/1977 | Benjamin | |
| 4,276,889 A | 7/1981 | Kuntz et al. | |
| 4,331,162 A | 5/1982 | Kuntz et al. | |
| 4,393,881 A | 7/1983 | Shah | |
| 4,492,258 A | 1/1985 | Lichtenstein et al. | |
| 4,494,581 A * | 1/1985 | Gordon | A61B 10/007 210/531 |
| 4,557,274 A | 12/1985 | Cawood | |
| 4,569,090 A | 2/1986 | Muller | |
| 4,769,215 A | 9/1988 | Ehrenkranz | |
| 4,852,560 A | 8/1989 | Hermann, Jr. et al. | |
| 5,038,109 A | 8/1991 | Goble et al. | |
| 5,069,878 A | 12/1991 | Ehrenkranz | |
| 5,279,330 A | 1/1994 | Debush | |
| 5,409,473 A | 4/1995 | Rosenshein | |
| 5,518,003 A | 5/1996 | Allan | |
| 5,711,310 A * | 1/1998 | Vinayagamoorthy | A61B 5/20 600/580 |
| 5,766,136 A | 6/1998 | Cawood | |
| 5,897,840 A | 4/1999 | Owens, Jr. et al. | |
| 6,054,099 A | 4/2000 | Levy | |
| 6,168,758 B1 | 1/2001 | Forsberg et al. | |
| 6,235,010 B1 | 5/2001 | Wilkinson et al. | |
| 6,277,646 B1 | 8/2001 | Guirguis et al. | |
| 6,680,027 B2 | 1/2004 | Kang et al. | |
| 6,726,879 B2 | 4/2004 | Ng et al. | |
| 6,750,007 B2 | 6/2004 | Canter et al. | |
| 7,195,602 B2 | 3/2007 | Yong et al. | |
| 7,547,298 B2 | 6/2009 | Lee et al. | |
| 7,819,821 B2 | 10/2010 | Forte et al. | |
| 7,871,385 B2 | 1/2011 | Levinson | |
| 8,043,230 B2 | 10/2011 | Deadwyler et al. | |
| 8,328,733 B2 | 12/2012 | Forte et al. | |
| 8,865,458 B2 | 10/2014 | Ramsey et al. | |
| 8,901,366 B2 | 12/2014 | Song et al. | |
| 9,155,525 B2 | 10/2015 | Lipinsky et al. | |
| 9,332,967 B2 | 5/2016 | Wu et al. | |
| 9,339,013 B1 | 5/2016 | Naponelli | |
| 9,352,314 B2 | 5/2016 | Vemalarajah | |
| 10,663,453 B2 | 5/2020 | Gouldy et al. | |
| 2004/0132091 A1 | 7/2004 | Ramsey et al. | |
| 2004/0267159 A1 | 12/2004 | Yong et al. | |
| 2008/0274014 A1 | 11/2008 | Jumonville et al. | |
| 2010/0159611 A1 | 6/2010 | Song et al. | |
| 2011/0237977 A1 | 9/2011 | Knight et al. | |
| 2014/0276216 A1 | 9/2014 | Lipinsky et al. | |
| 2015/0009502 A1 | 1/2015 | Drury | |
| 2015/0223784 A1* | 8/2015 | Van Damme | A61B 10/007 73/864.63 |
| 2017/0296155 A1 | 10/2017 | Exosome | |
| 2018/0078191 A1 | 3/2018 | Hall et al. | |
| 2020/0085378 A1 | 3/2020 | Burnett et al. | |

FOREIGN PATENT DOCUMENTS

| | | |
|---|---|---|
| JP | 4331162 B2 | 9/2009 |
| JP | 4393881 B2 | 1/2010 |
| JP | 4769215 B2 | 9/2011 |
| JP | 4852560 B2 | 1/2012 |
| JP | 5069878 B2 | 11/2012 |
| JP | 5279330 B2 | 9/2013 |
| JP | 5711310 B2 | 4/2015 |
| JP | 5766136 B2 | 8/2015 |
| JP | 5897840 B2 | 3/2016 |
| JP | 6168758 B2 | 7/2017 |
| JP | 6277646 B2 | 2/2018 |
| JP | 6680027 B2 | 4/2020 |

OTHER PUBLICATIONS

Adams WM, et al. Racial and sex differences in 24 hour urinary hydration markers among male and female emerging adults: A pilot study. Nutrients 2020; 12: 1068.

Adams, J. D., et al. "Combining urine color and void number to assess hydration in adults and children." European Journal of Clinical Nutrition 75.8 (2021): 1262-1266.

Armstrong LE, et al. Human hydration indices: Acute and longitudinal reference values. Int J Sport Nutr Exerc Metab 2010; 20: 145-53.

Armstrong LE, et al. Urinary indices during dehydration, exercise, and rehydration. Int J Sport Nutr Exerc Metab 1998; 8: 345-355.

Armstrong LE, et al. Urinary indices of hydration status. Int J Sport Nutr 1994; 4: 265-79.

Armstrong LE, Johnson EC, Kunces LJ et al (2014) Drinking to thirst versus drinking ad libitum during road cycling. J Athl Train 49:624-631. https://doi.org/10.4085/1062-6050-49.3.85.

Armstrong, LE, et al. An empirical method to determine inadequacy of dietary water. Nutrition 2016, 32, 79-82.

Arnaoutis G, et al. Fluid balance during training in elite young athletes of different sports. J Strength Cond Res 2015; 29: 3447-3452.

Baerheim, et al. {1992). Evaluation of urine sampling technique: Bacterial contamination of samples from women students. The British Journal of General Practice : The Journal of the Royal College of General Practitioners, 42(359), 241-243.

Baron S, et al. Assessment of hydration status in a large population. Br J Nutr 2015; 113: 147-158.

Belasco R, et al. The Effect of Hydration on Urine Color Objectively Evaluated in CIE L*a*b* Color Space. Front Nutr 2020; 7: 576974.

Blake, et al. (2006). Effect of Perineal Cleansing on Contamination Rate of Mid-stream Urine Culture. Journal of Pediatric and Adolescent Gynecology, 19(1), 31-34.

Boshell, B.R., et al. (1958). A screening method for the evaluation of urinary tract infections in female patients without catheterization. Annals of Internal Medicine. 48:1040-1045. doi: 10.7326/0003-4819-48-5-1040.

Bottin JH, et al. Equivalence of afternoon spot and 24-h urinary hydration biomarkers in free-living healthy adults. Eur J Clin Nutr 2016; 70: 904-907.

Campa, F. et al. The effects of dehydration on metabolic and neuromuscular functionality during cycling. Int. J. Environ. Res. Public Health 2020, 17, 1161.

Carpenter, S. (2001). Sights unseen. APA Monitor, 32, 54-57.

Charlwood. Mittstrom Mid Stream Urine Device. Version dated Jan. 27, 2020. Available online at http://charlwood.com.au/mittstrom-mid-stream-urine-device/ (2 pages).

Cheuvront SN, et al. Biological variation and diagnostic accuracy of dehydration assessment markers. Am J Clin Nutr 2010; 92: 565-73.

Ellis LA, et al. Effects of three oral nutritional supplements on human hydration indices. Int J Sport Nutr Exerc Metab 2016; 26: 356-362.

Fisher Scientific. Midstream Urine Collection Kits Product Listing Page. Version dated Mar. 7, 2023. Available online at https://www.fishersci.com/us/en/products/I9C8KT9A/midstream-urine-collection-kits.html (2 pages).

Fortes MB, et al. Is this elderly patient dehydrated? Diagnostic accuracy of hydration assessment using physical signs, Urine, and saliva markers. J Am Med Dir Assoc 2015; 16: 221-228.

Frazee, B., et al. (2012). Urine collection in the emergency department: What really happens in there? The Western Journal of Emergency Medicine, 13(5), 401-5.

Frazee, et al. (2015). Abnormal Urinalysis Results Are Common, Regardless of Specimen Collection Technique, in Women Without Urinary Tract Infections. Journal of Emergency Medicine, 48(6), 706-711.

(56) References Cited

OTHER PUBLICATIONS

Herslund, M. B. et al. (2003). Looked-but-failed-to-see-errors in traffic. Accident Analysis and Prevention, 35, 885-891.
Hew-Butler TD, et al. Dehydration is how you define it: Comparison of 318 blood and urine athlete spot checks. BMJ Open Sport Exerc Med 2018;4:e000297.
Holm, A., et al. (2016). Urine sampling techniques in symptomatic primary-care patients: A diagnostic accuracy review. BMC Family Practice, 17(1), 72.
International Preliminary Report on Patentability for Application No. PCT/US2021/015741 dated Jul. 28, 2022 (10 pages).
Jacob, K. et al. (2018). Use of a midstream clean catch mobile application did not lower urine contamination rates in an ED. American Journal of Emergency Medicine, 36(1), 61-65.
Kavouras SA, et al. Educational intervention on water intake improves hydration status and enhances exercise performance in athletic youth. Scand. J. Med. Sci. Sport. 2012, 22, 684-689.
Kavouras SA, et al. Validation of a urine color scale for assessment of urine osmolality in healthy children. Eur J Nutr 2016; 55: 907-915.
Kavouras SA. Hydration, dehydration, underhydration, optimal hydration: are we barking up the wrong tree? Eur J Nutr 2019; 58: 471-473.
Kenefick, R.W.; et al. Hydration for recreational sport and physical activity. Nutr. Rev. 2012, 70, S137-S142.
Kenefick, R.W.; et al. Quantification of chromatographic effects of Vitamin B supplementation in urine and implications for hydration assessment. J. Appl. Physiol. 2015, 119, 110-115.
Kenney, E.L.; et al. Prevalence of inadequate hydration among US children and disparities by gender and Race/Ethnicity: National Health and Nutrition Examination Survey, 2009-2012. Am. J. Public Health 2015, 105, e113-e118.
Kostelnik, S.B.; et al. The validity of urine color as a hydration biomarker within the general adult population and athletes: A systematic review. J. Am. Coll. Nutr. 2020, 40, 172-179.
Arocco, M., et al. (2016). Effectiveness of Preanalytic Practices on Contamination and Diagnostic Accuracy of Urine Cultures: A Laboratory Medicine Best Practices Systematic Review and Meta-analysis. Clinical Microbiology Reviews, 29(1), 105-147.
Laughery, K. R., et al. "Modeling Human Performance in Complex Systems." Handbook of Human Factors and Ergonomics, 4th Edition, John Wiley & Sons, 2012, pp. 2-2.
Lee, J. D., et al. (2017). Designing for People: An Introduction to Human Factors Engineering (3d ed.). Charleston, SC: Create Space. ISBN: 1539808009.
Maher, et al. (2017). The Effect of Written Posted Instructions on Collection of Clean-Catch Urine Specimens in the Emergency Department. Journal of Emergency Medicine, 52(5), 639-644.
Martin WF, et al. Effects of dietary protein intake on indexes of hydration. J Am Diet Assoc 2006; 106: 587-589.
McDermott BP, et al. National Athletic Trainers' Association position statement: Fluid replacement for the physically active. J Athl Train 2017; 52: 877-895.
McKenzie AL, Muñoz CX, Ellis LA et al (2017) Urine color as an indicator of urine concentration in pregnant and lactating women. Eur J Nutr 56:355-362. https://doi.org/10.1007/s00394-015-1085-9.
Mentes JC, et al. Use of a urine color chart to monitor hydration status in nursing home residents. Biol Res Nurs 2006; 7: 197-203.
Olzinski S, et al. Hydration status and fluid needs of division I female collegiate athletes exercising indoors and outdoors. Sports 2019; 7: 155.
Perrier ET, et al. "Twenty-four-hour urine osmolality as a physiological index of adequate water intake." Disease markers 2015 (2015).

Perrier ET, et al. Circadian variation and responsiveness of hydration biomarkers to changes in daily water intake. Eur. J. Appl. Physiol. 2013, 113, 2143-2151.
International Search Report and Written Opinion for International Patent Application No. PCT/US2021/015741, dated Apr. 23, 2021 (12 pages).
Perrier ET, et al. Criterion values for urine-specific gravity and urine color representing adequate water intake in healthy adults. Eur J Clin Nutr 2017; 71: 561-563.
Reis, J.F.; et al. Bioimpedance vector patterns changes in response to swimming training: An ecological approach. Int. J. Environ. Res. Public Health 2020, 17, 4851.
Rodrigues S, et al. Validation analysis of a geriatric dehydration screening tool in community-dwelling and institutionalized elderly people. Int J Environ Res Public Health 2015; 12: 2700-2717.
Sawka MN, et al. (2007). American College of Sports Medicine position stand. Exercise and fluid replacement. Medicine and science in sports and exercise, 39(2), 377.
Schappert, S., et al. (2011). Ambulatory medical care utilization estimates for 2007. Vital and Health Statistics. Series 13, Data from the National Health Survey, (169), 1-38.
Schulte, F., et al. (Nov. 6, 2017). Liquid Gold: Pain Doctors Soak Up Profits By Screening Urine For Drugs. Retrieved from https://khn.org/news/liquid-gold-pain-doctors-soak-up-profits-by-screening-urine-for-drugs/.
Simmering, J. E, et al. (2017). The Increase in Hospitalizations for Urinary Tract Infections and the Associated Costs in the United States, 1998-2011. Open Forum Infectious Diseases, 4(1), Ofw281.
Sliney DH. What is light? The visible spectrum and beyond. Eye 2016; 30: 222-229.
Sommerfield LM, et al. Validity of urine specific gravity when compared with plasma osmolality as a measure of hydration status in male and female NCAA collegiate athletes. J Strength Cond Res 2016; 30: 2219-2225.
Stookey, J.D.; et al. What is the cell hydration status of healthy children in the USA? Preliminary data on urine osmolality and water intake. Public Health Nutr. 2012, 15, 2148-2156.
Suh, H.G.; et al. Afternoon urine osmolality is equivalent to 24 h for hydration assessment in healthy children. Eur. J. Clin. Nutr. 2020, 74, 884-890.
Wakefield B, et al. Monitoring hydration status in elderly veterans. West J Nurs Res 2002; 24: 132-142.
Wardenaar, F. C., et al. "A lavatory urine color (LUC) chart method can identify hypohydration in a physically active population." European Journal of Nutrition 60.5 (2021): 2795-2805.
Wardenaar, F. C., et al. "Athletes' self-assessment of urine color using two color charts to determine urine concentration." International journal of environmental research and public health 18.8 (2021): 4126.
Wardenaar, F., et al. "Validity of Urine Color Scoring Using Different Light Conditions and Scoring Techniques to Assess Urine Concentration." Journal of Athletic Training 57.2 (2022): 191-198.
Whiz Products. The Whiz Midstream. Version dated Dec. 26, 2019. Available online at https://web.archive.org/web/20191226163811/http://www.whizproducts.co.uk/the-whiz-midstream/ (4 pages).
Wickens, C., et al. (2008). Applied attention theory. Boca Raton: CRC Press.
Zhang N, et al. Urine color for assessment of dehydration among college men students in Hebei, China—a cross-sectional study. Asia Pac J Clin Nutr 2017; 26: 788-793.
Zweig MH, Campbell G {1993) Receiver-operating characteristic (ROC) plots: a fundamental evaluation tool in clinical medicine. Clin Chem 39:561-577.

\* cited by examiner

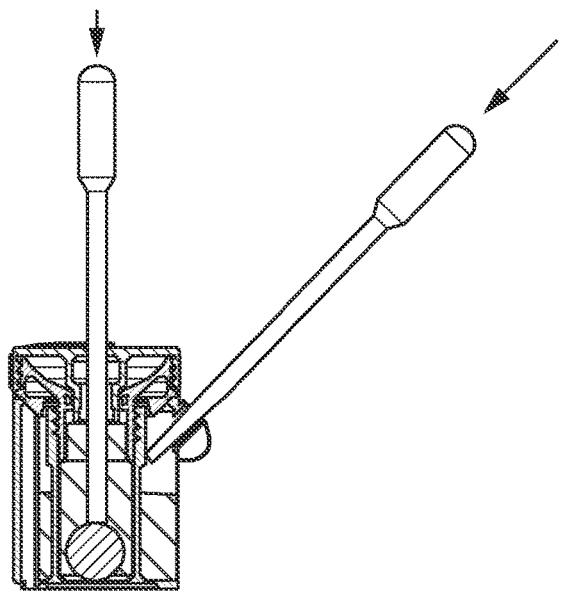 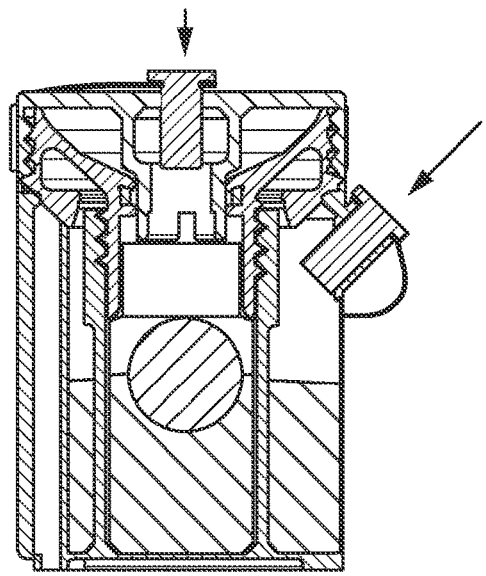
FIG. 19A        FIG. 19B
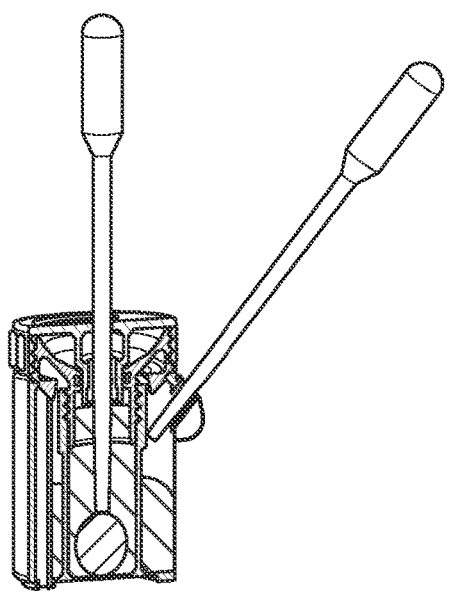 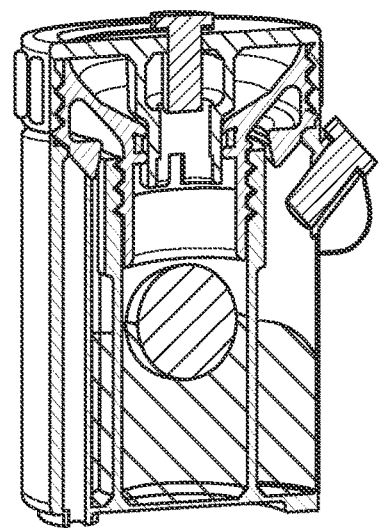
FIG. 20A        FIG. 20B

URINE COLLECTION, STORAGE, AND TESTING ASSEMBLY

CROSS-REFERENCE TO RELATED APPLICATIONS

This application is a non-provisional of 62/968,758, filed on Jan. 31, 2020, the contents of which is incorporated herein by reference.

BACKGROUND

Conventional methods of urine sample collection are cognitively and physically demanding, and therefore often lead to contaminated samples and erroneous results.

SUMMARY

In one embodiment, a urine collection assembly includes a container; a funnel removably coupled to the container, the funnel in fluid communication with the container; a first collection chamber in selective communication with the funnel; a valve configured to allow selective communication between the first collection chamber and the funnel; a second collection chamber in selective communication with the funnel; and a lid removably coupleable to the funnel.

In another embodiment, a urine collection assembly includes a container including a first collection chamber, a second collection chamber, and a channel that is in selective fluid communication with the second collection chamber. The channel has a first opening adjacent a first end of the container and a second opening adjacent a second end of the container. The urine collection assembly further includes a funnel movably coupled to the container and in selective fluid communication with the first collection chamber and the second collection chamber. The funnel is movable relative to the container between a first position in which the second collection chamber is in fluid communication with the channel and a second position in which fluid communication between the first collection chamber and the second collection chamber is prevented. The urine collection assembly further includes a valve configured to allow selective communication between the first collection chamber and the funnel and to allow selective communication between the second collection chamber and the funnel. The urine collection assembly further includes a lid removably coupleable to the funnel to move the container from the first position to the second position. In some embodiments, a saddle may be removably coupleable to the funnel and configured to guide urine into the container.

In another embodiment, a urine collection assembly includes a container including a first collection chamber and a second collection chamber, a funnel removably coupled to the container. The funnel is in selective fluid communication with the first collection chamber and the second collection chamber. The urine collection assembly also includes a valve positioned within the first collection chamber and movable between a first position and a second position. A lid is also removably coupleable to the funnel. When the valve is in the first position, the first collection chamber is in communication with funnel, and when the valve is in the second position, fluid communication between the first collection chamber and the funnel is prevented and the second collection chamber is in communication with funnel the funnel. In some embodiments, a saddle may be removably coupleable to the funnel and configured to guide urine into the container.

In another embodiment, a urine collection assembly includes a container, a funnel removably coupled to the container. The funnel is in fluid communication with the container. A first collection chamber of the container is in selective communication with the funnel for automatically collecting a first catch of urine. A valve is configured to allow selective communication between the first collection chamber and the funnel. A second collection chamber of the container is in selective communication with the funnel for automatically collecting a second catch of urine. A lid is removably coupleable to the funnel. In some embodiments, a saddle may be removably coupleable to the funnel and configured to guide urine into the container.

Other aspects of the invention will become apparent by consideration of the detailed description and accompanying drawings.

BRIEF DESCRIPTION OF THE DRAWINGS

FIG. 19A illustrates a side view of a first step of the process of extracting portion of the urine sample from the urine collection assembly illustrated in the embodiments of FIGS. 1-3, 10A, and 11-16.

FIG. 19B illustrates a side view of a second step of the process of extracting portion of the urine sample from the urine collection assembly illustrated in the embodiments of FIGS. 1-3, 10A, and 11-16.

FIG. 20A illustrates a perspective view of the first step of the process of extracting portion of the urine sample from the urine collection assembly illustrated in the embodiments of FIGS. 1-3, 10A, and 11-16.

FIG. 20B illustrates a perspective view of the second step of the process of extracting portion of the urine sample from the urine collection assembly illustrated in the embodiments of FIGS. 1-3, 10A, and 11-16.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 7:
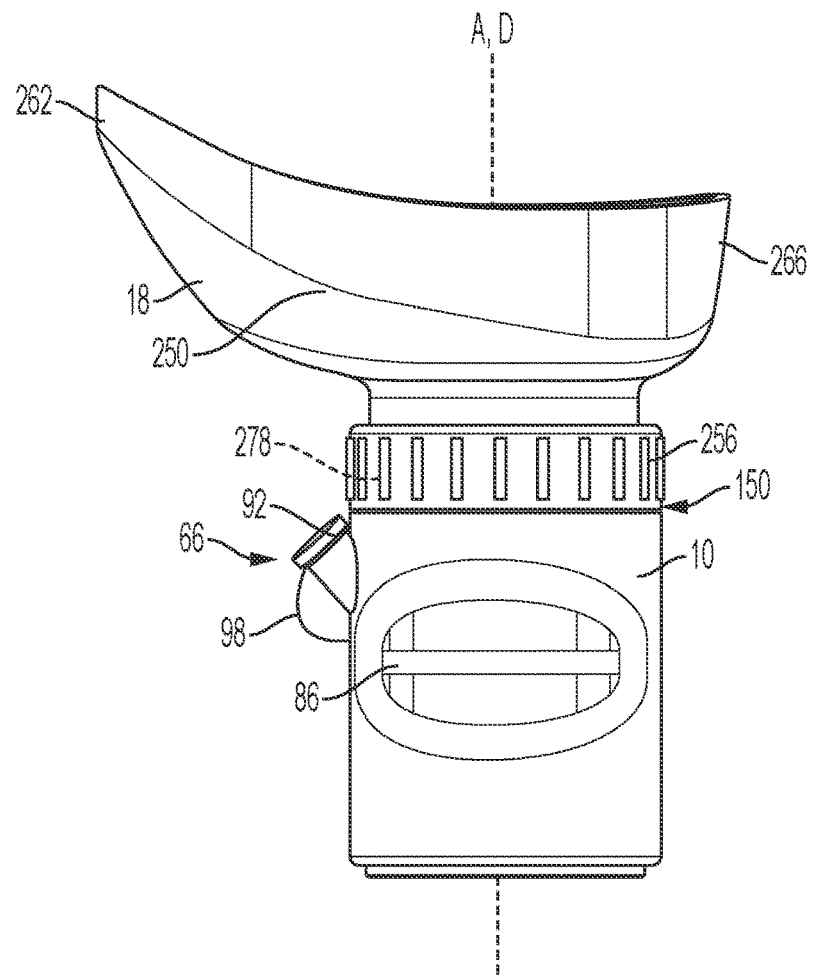
FIG. 7 illustrates a side view of the urine collection assembly of FIG. 1 including a saddle according to one embodiment coupled to the container, rather than the lid.
Figure 8:
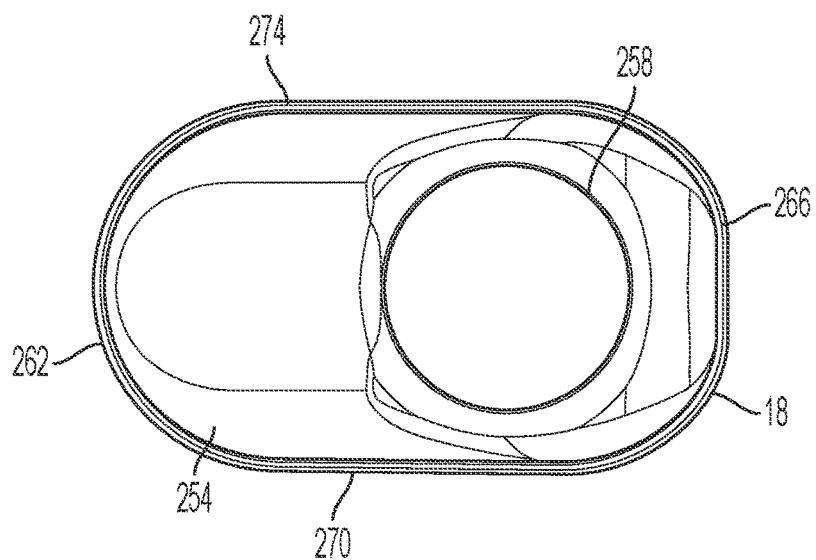
FIG. 8 is a top view of the saddle of FIG. 7.
Figure 9A:
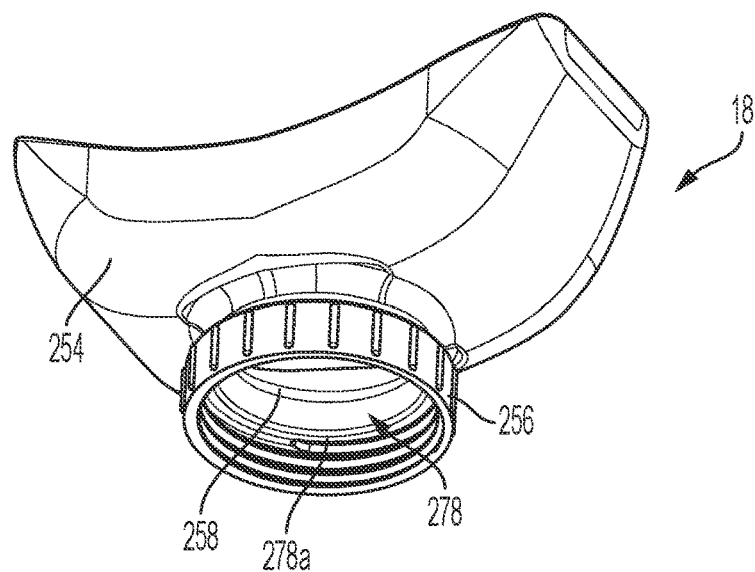
FIG. 9A illustrates a perspective view of a saddle according to another embodiment that is configured for use with the urine collection assembly of FIG. 1.
Figure 9B:
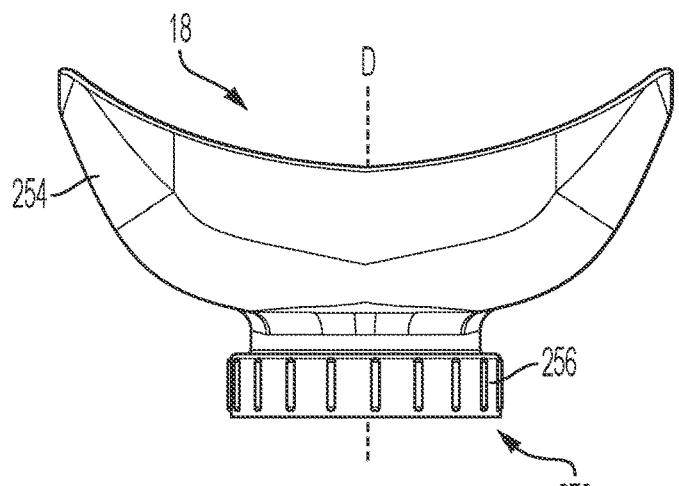
FIG. 9B illustrates a side view of the saddle of FIG. 9A.
Figure 9C:
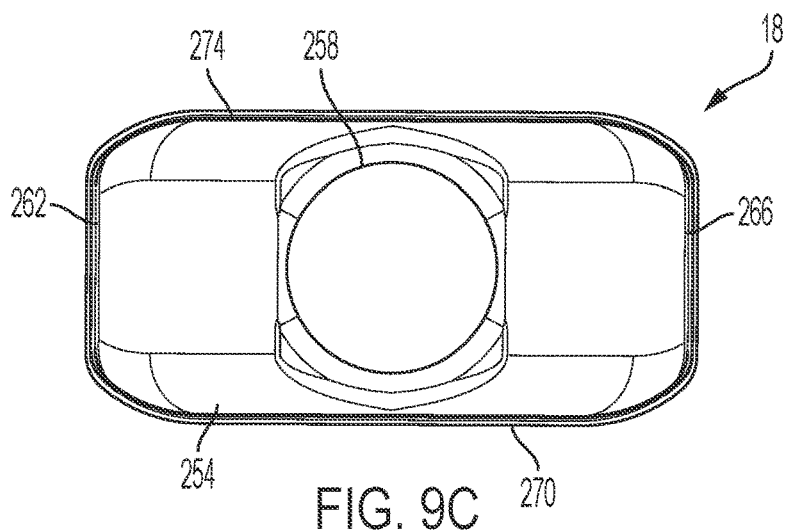
FIG. 9C illustrates a top view of the saddle of FIG. 9A.

FIGS. 1-8 illustrate a urine collection assembly according to one embodiment. The urine collection assembly includes a container 10, a lid 14 (FIGS. 1-3), and a saddle 18 (FIGS. 7-8). The lid 14 and the saddle 18 are removably coupleable to the container 10. The saddle 18 is optional for use and may be used by males and females when collecting a urine sample.

Figure 1:
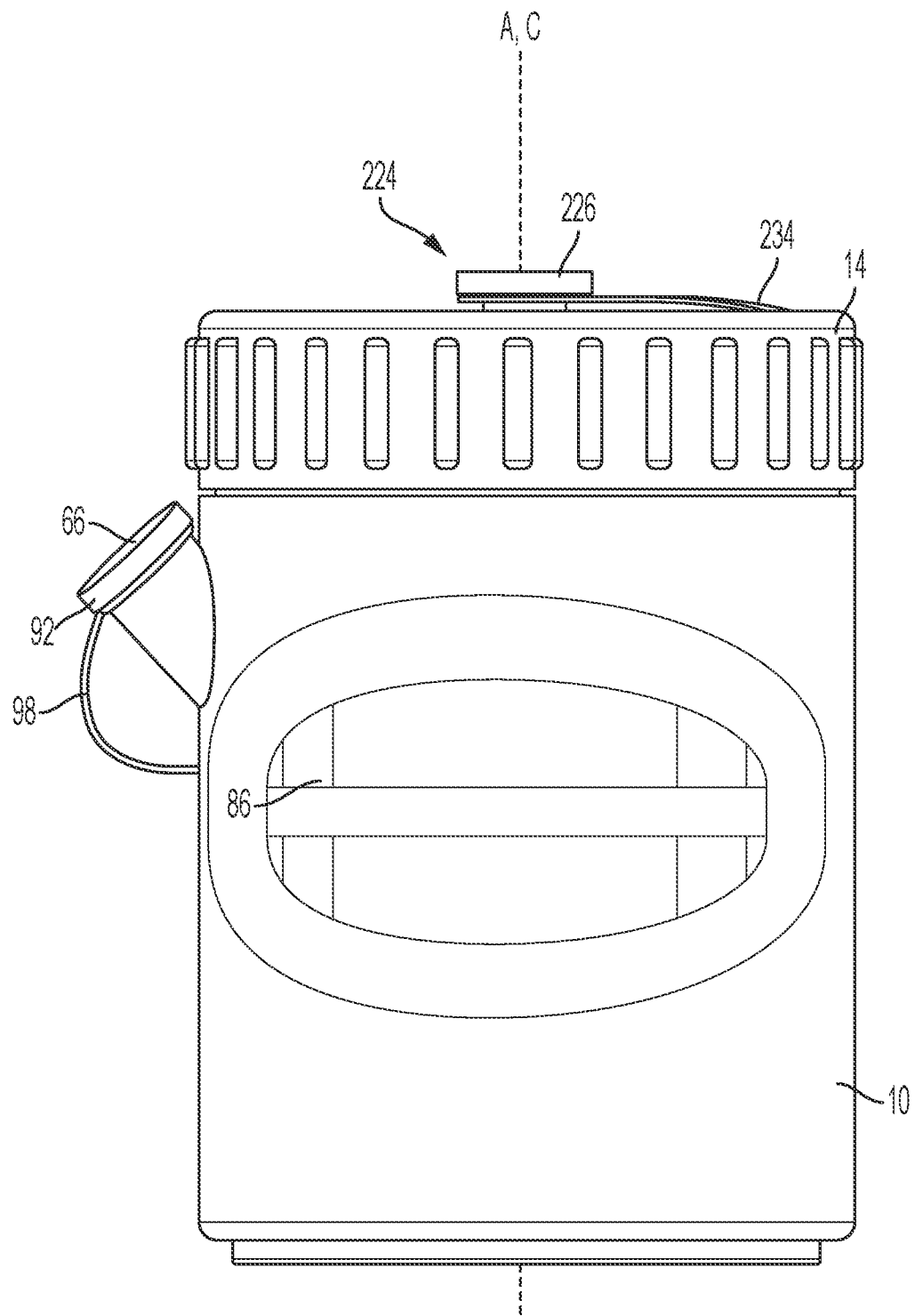
FIG. 1 illustrates a side view of a urine collection assembly according to one embodiment and including a container and a lid.
Figure 2:
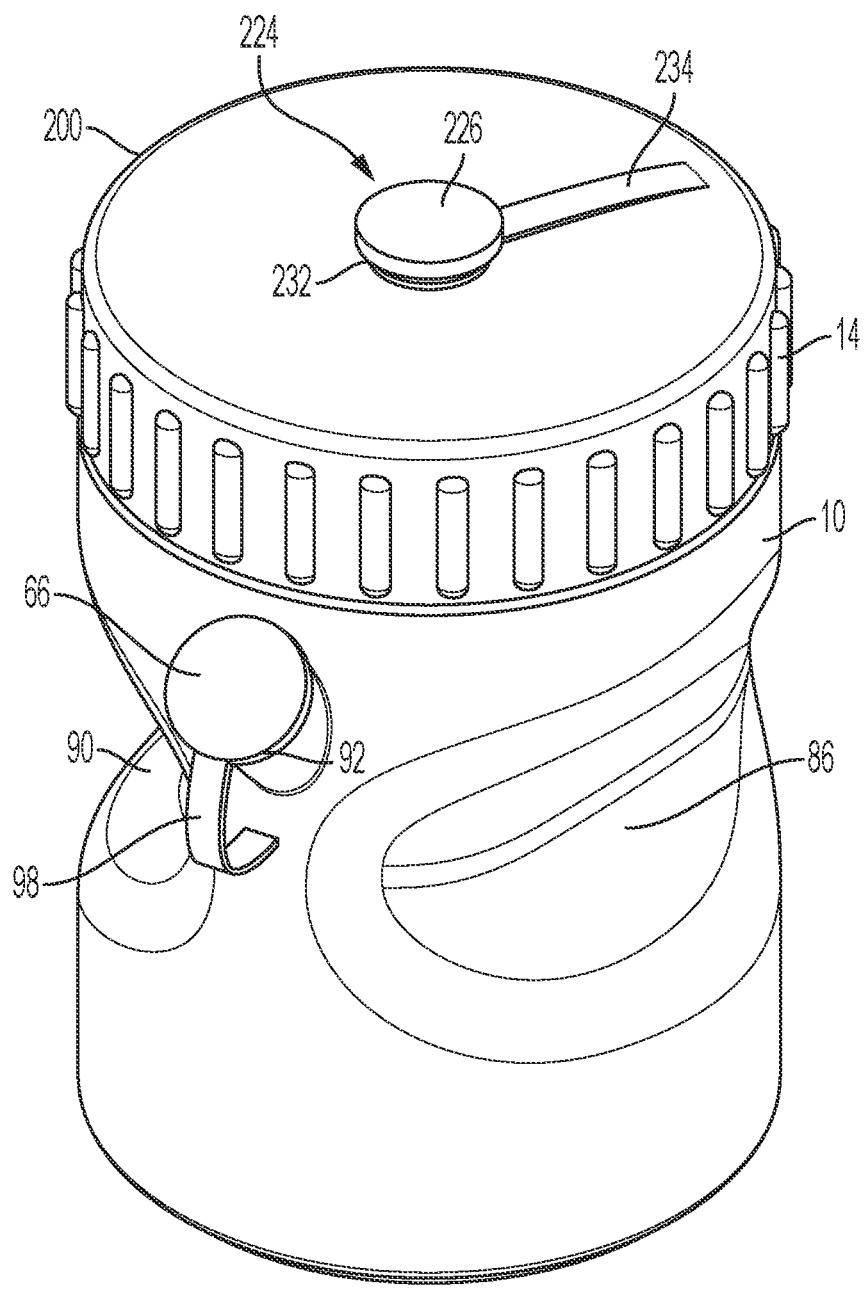
FIG. 2 illustrates a perspective view of the urine collection assembly of FIG. 1.
Figure 3:
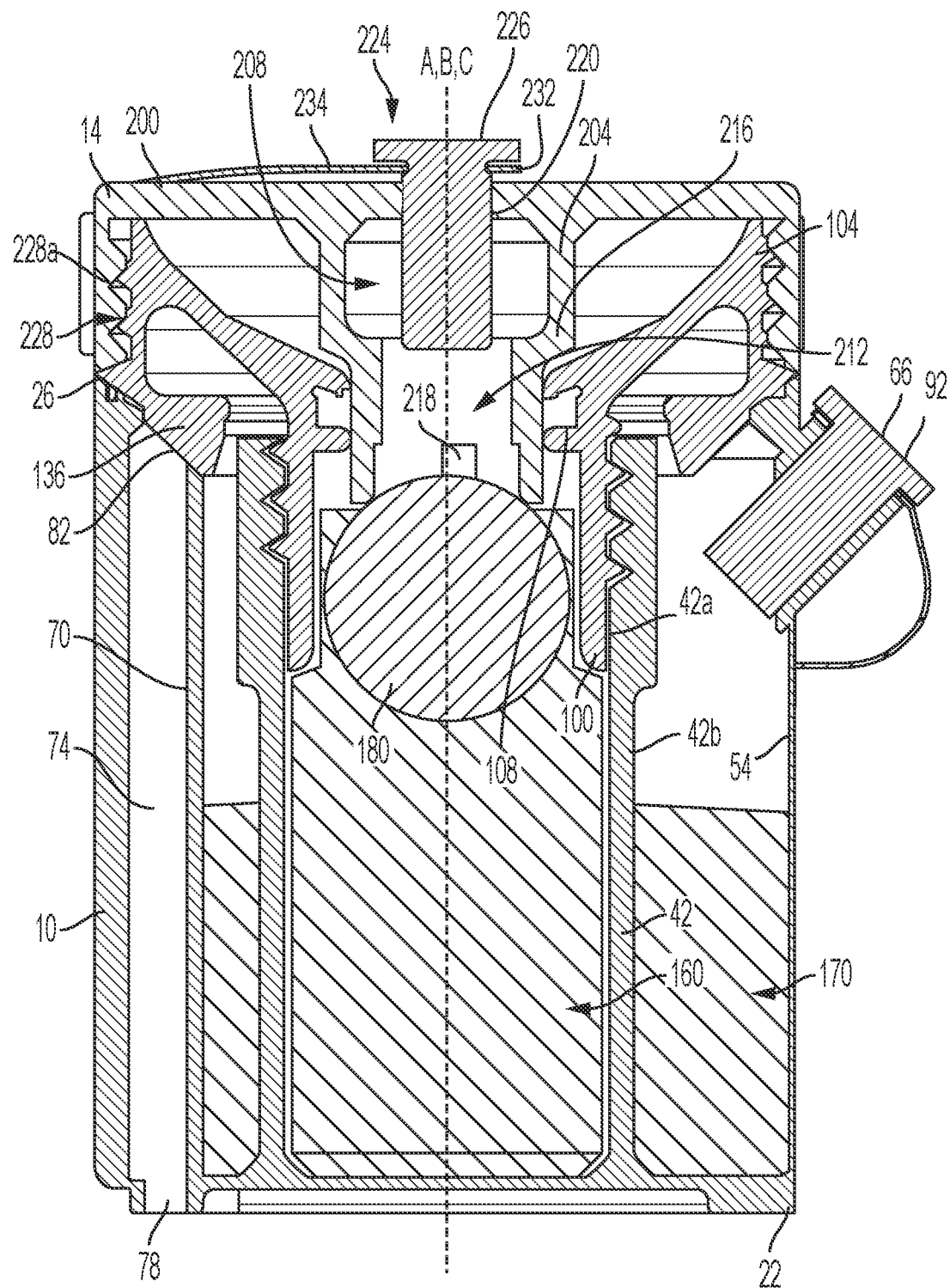
FIG. 3 illustrates a cross-sectional view of the urine collection assembly of FIG. 1 taken along a longitudinal axis.
Figure 4:
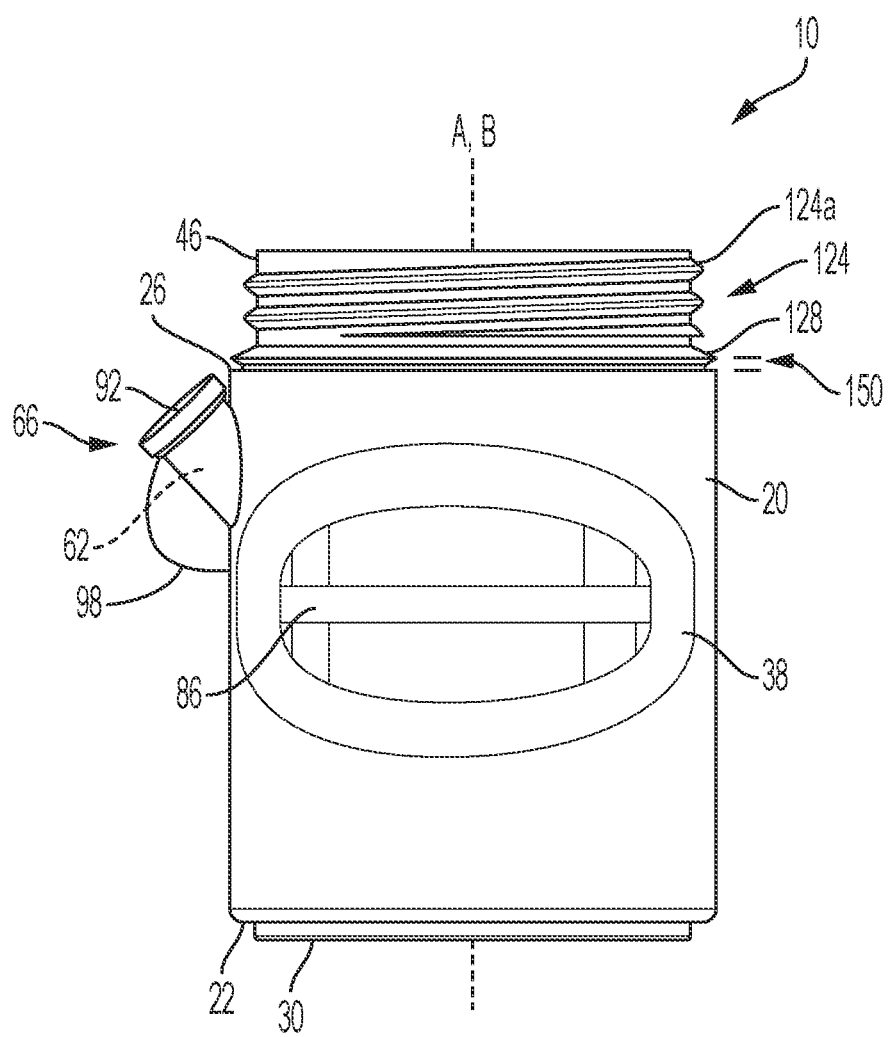
FIG. 4 illustrates a side view of the container of FIG. 1.
Figure 5:
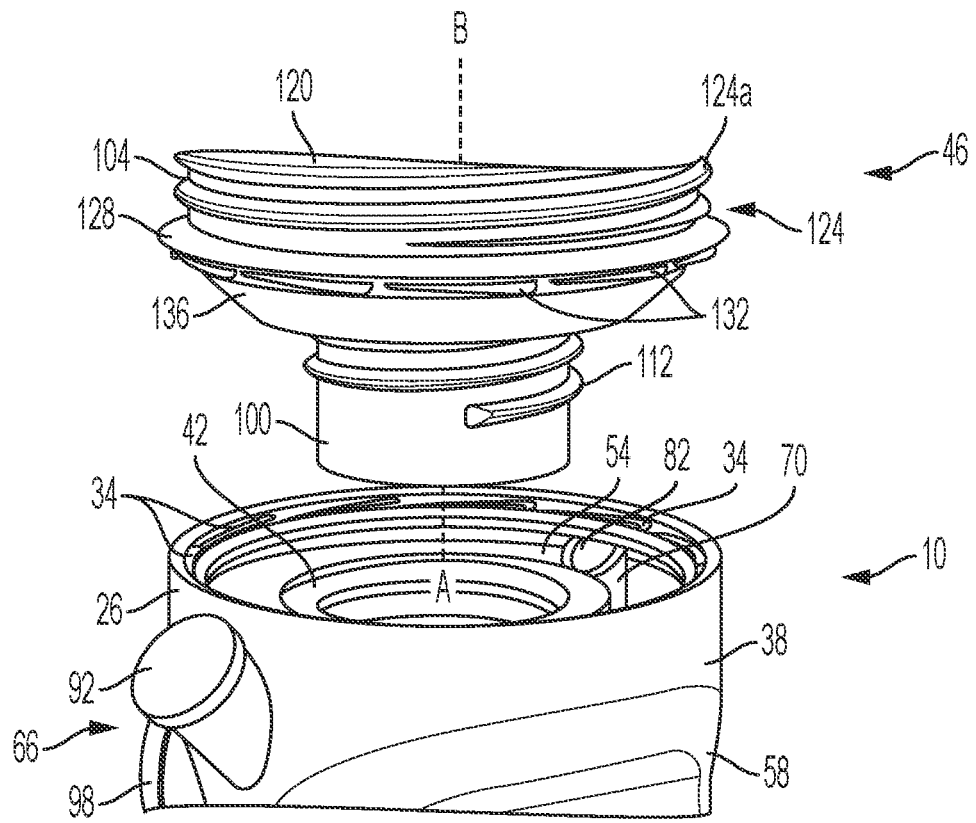
FIG. 5 illustrates a partially exploded view of the container of FIG. 1.
Figures 6A, 6B:
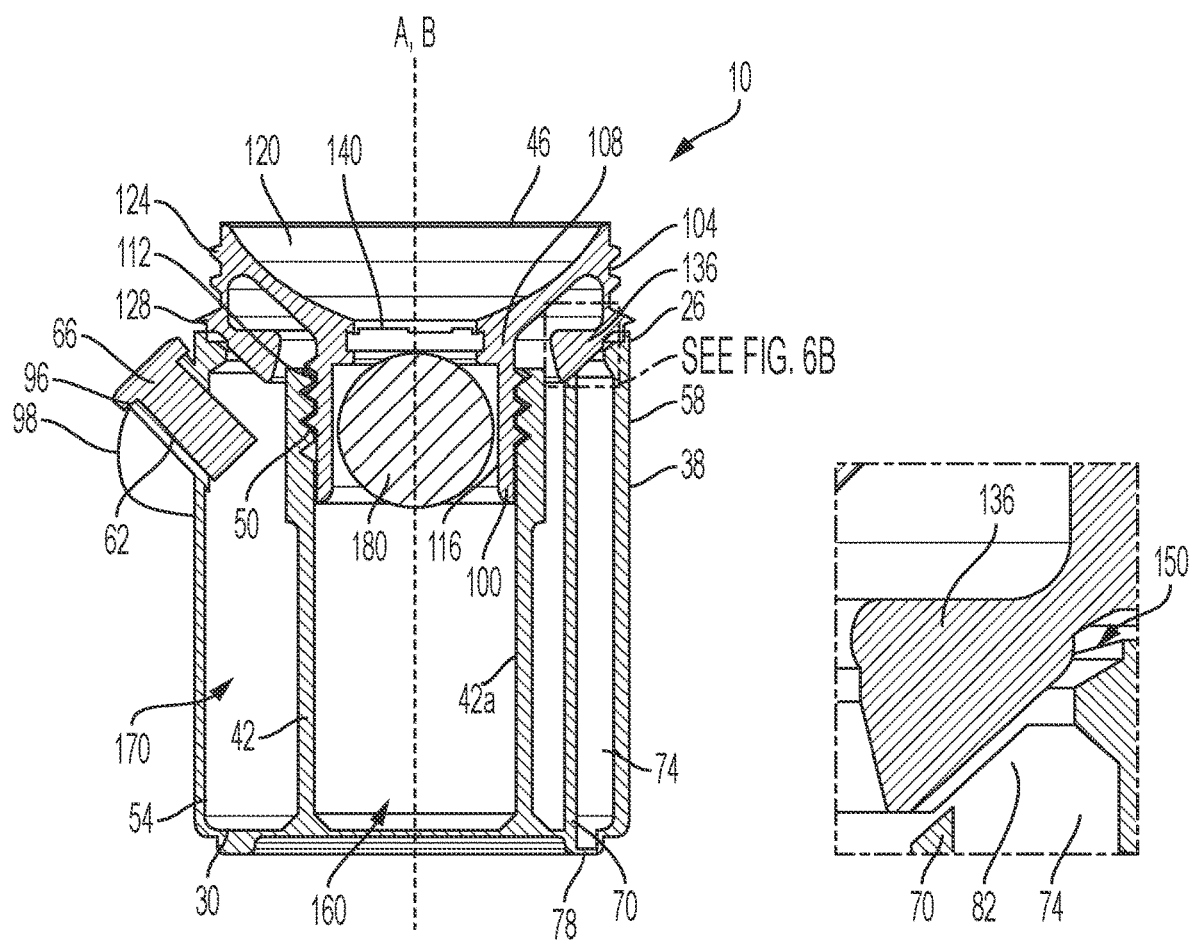
FIG. 6A illustrates a cross-sectional view of the container of FIG. 1 along the longitudinal axis.
FIG. 6B illustrates a detailed view of a portion of FIG. 6A.

With respect to FIGS. 3-6B in particular, the container 10 includes a body 20 that has a longitudinal axis A, a first end 22, a second end 26 opposite the first end 22, a base 30 positioned at the first end 22, locking elements 34 (e.g., projections, FIG. 5) positioned circumferentially about the second end 26, an outer wall 38 integrally formed with (or otherwise coupled) and extending from the base 30 between the first end 22 and the second end 26, a first inner wall 42 integrally formed with (or otherwise coupled) and extending from the base 30 and extending from the first end 22 toward the second end 26. A closure element 46 is coupled to the first end 22 of the body 22. The inner wall 42 is substantially cylindrical and includes a threaded portion 50 on a portion of an inner surface 42a (FIG. 3). The outer wall 38 includes an inner surface 54 and an outer surface 58. The inner wall 42 is spaced a distance from the inner surface 54 of the outer wall 38 within the body 20. An aperture 62 (FIG. 6A) extends through the outer wall 38 from the outer surface 58 to the inner surface 54 and removably receives a plug 66.

Figure 10A:
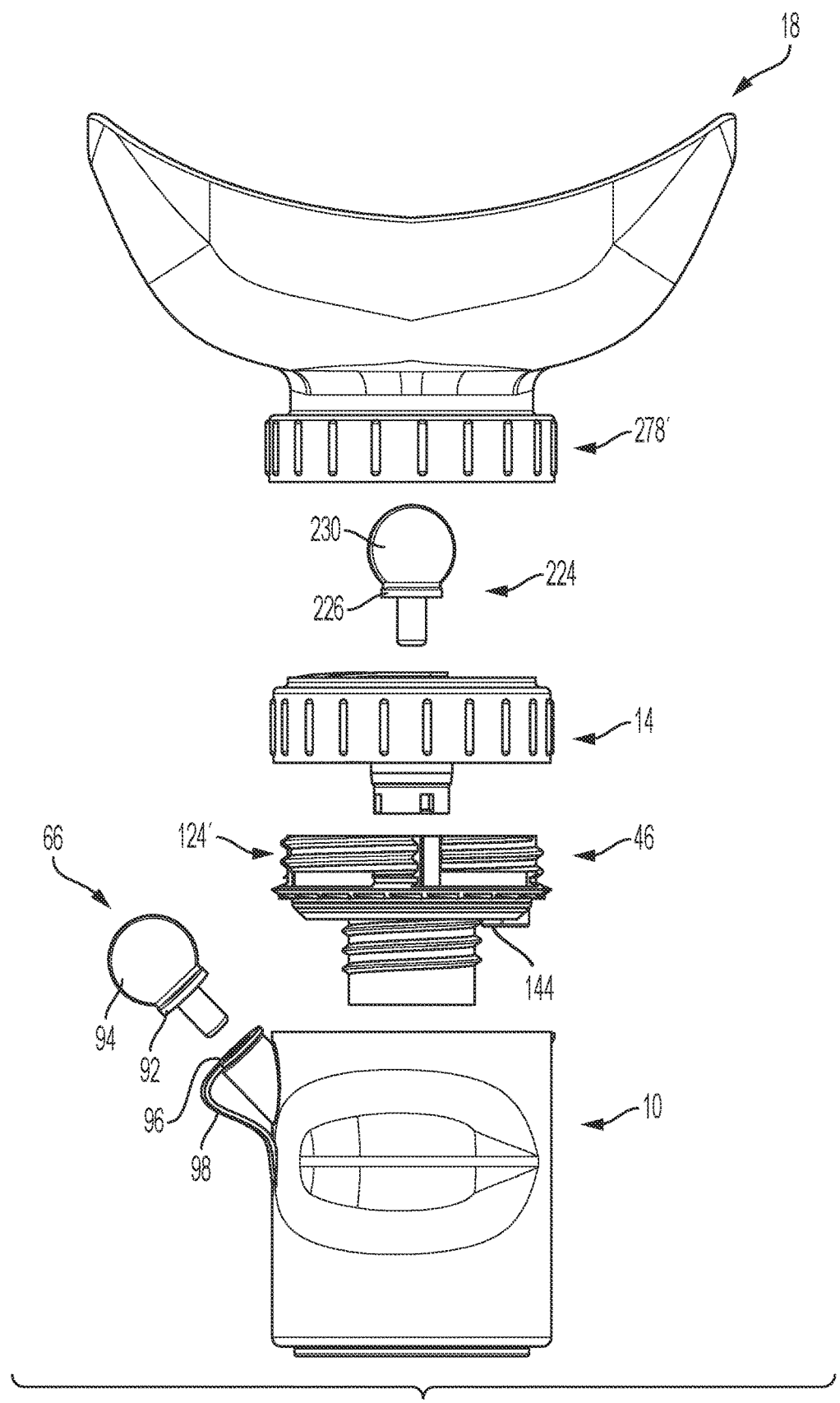
FIG. 10A illustrates a side exploded view of a urine collection assembly according to another embodiment and including a lid, a container, and a saddle.
Figure 10B:
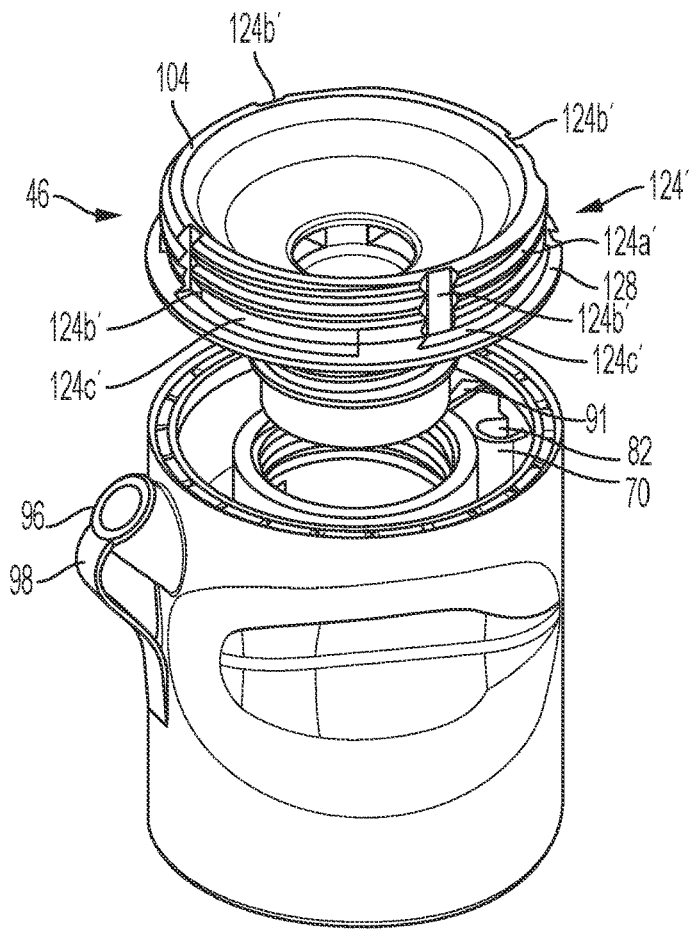
FIG. 10B illustrates a perspective exploded view of a container of FIG. 10A.
Figure 10C:
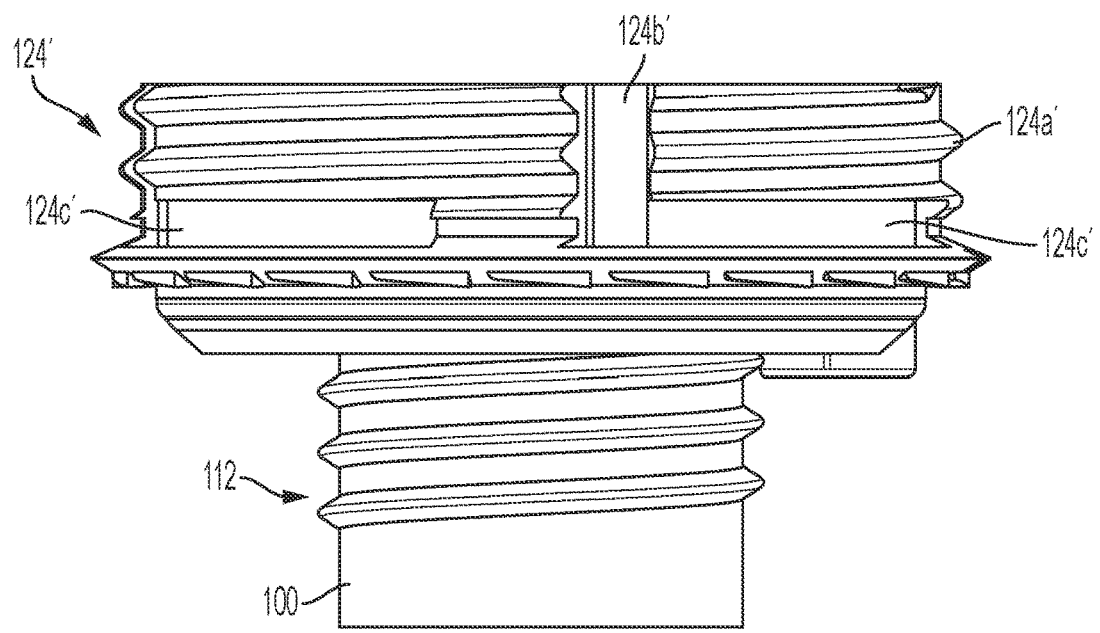
FIG. 10C illustrates a side view of a portion of the container of FIG. 10A.
Figure 10D:
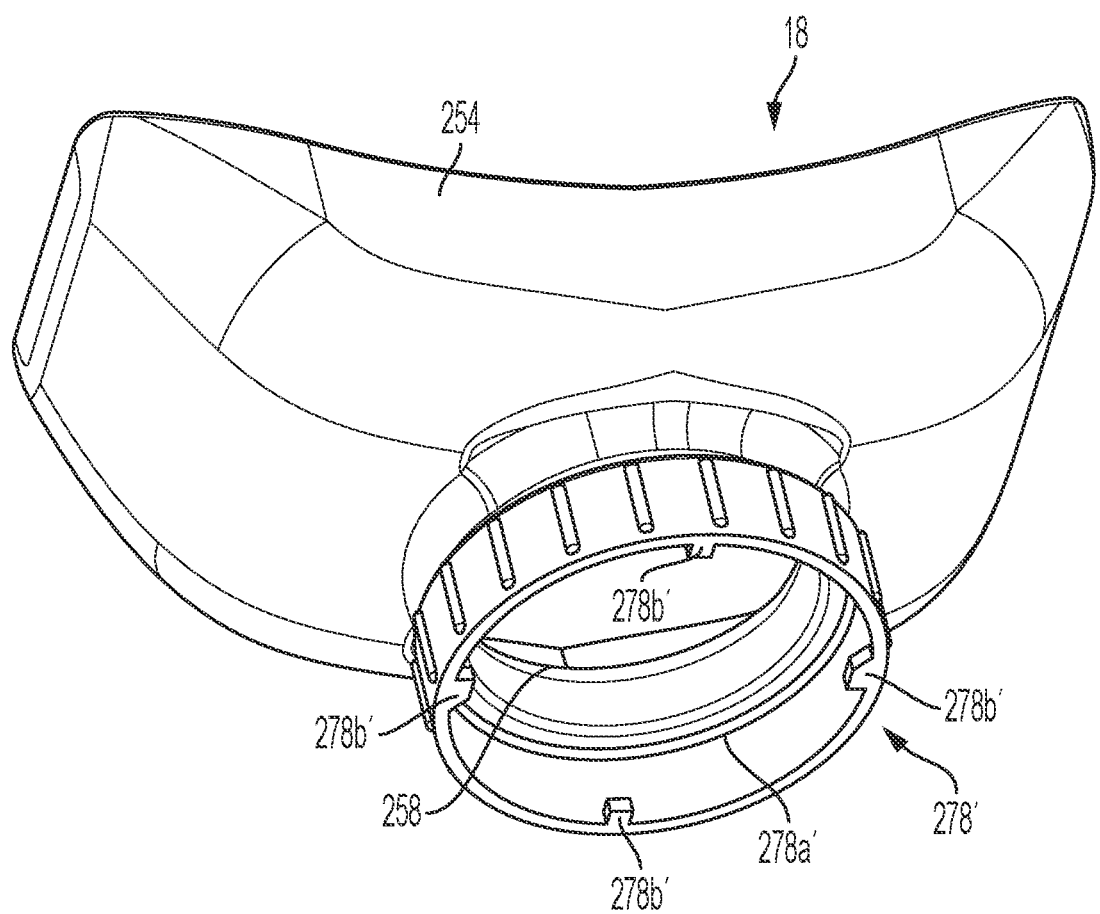
FIG. 10D illustrates a perspective view of the saddle of FIG. 10A.
Figure 11:
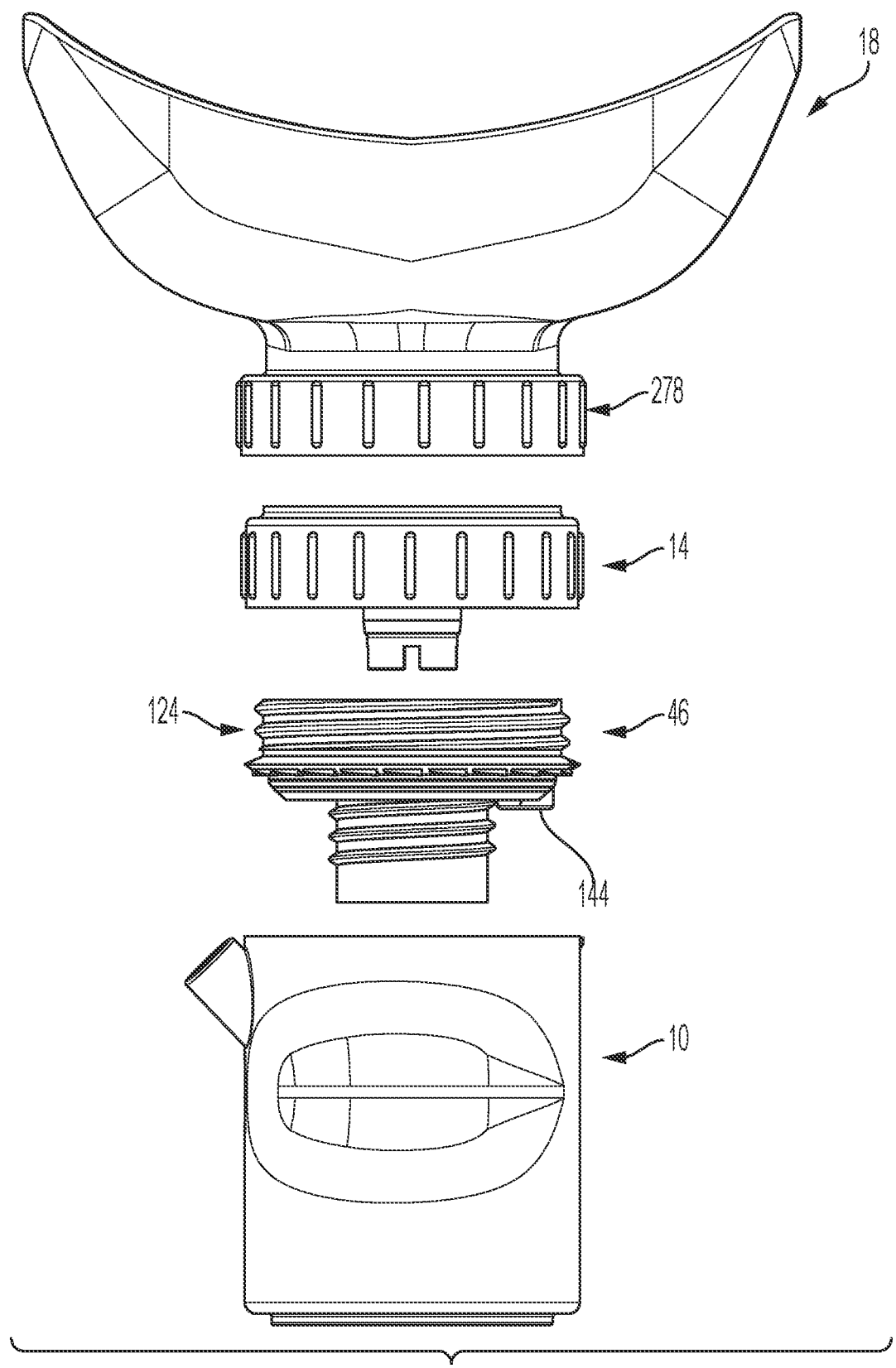
FIG. 11 illustrates a side exploded view of a urine collection assembly according to an embodiment and including a container, a lid and a saddle.
Figure 12:
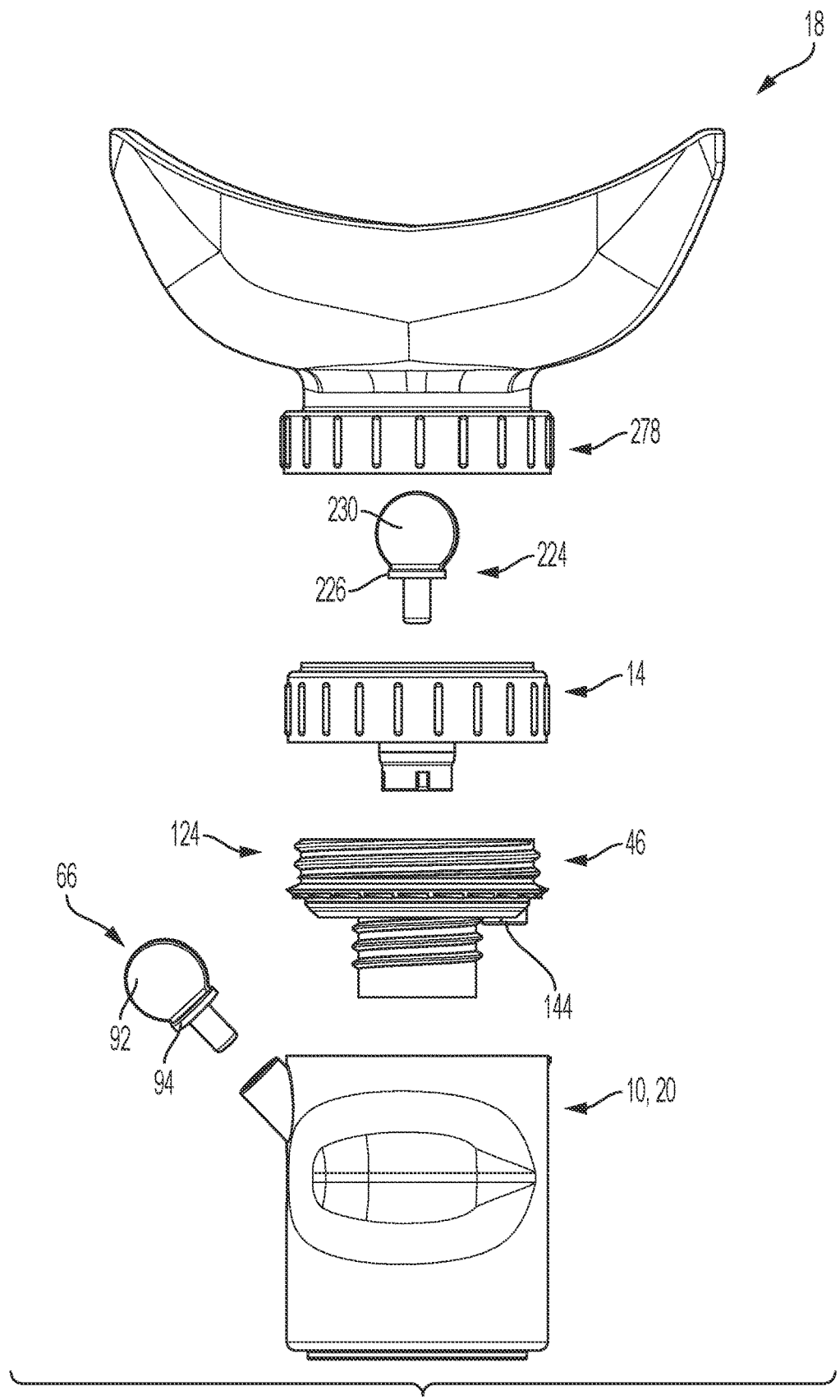
FIG. 12 illustrates a side exploded view of a urine collection assembly according to another embodiment and including a container, a lid and a saddle.
Figure 13:
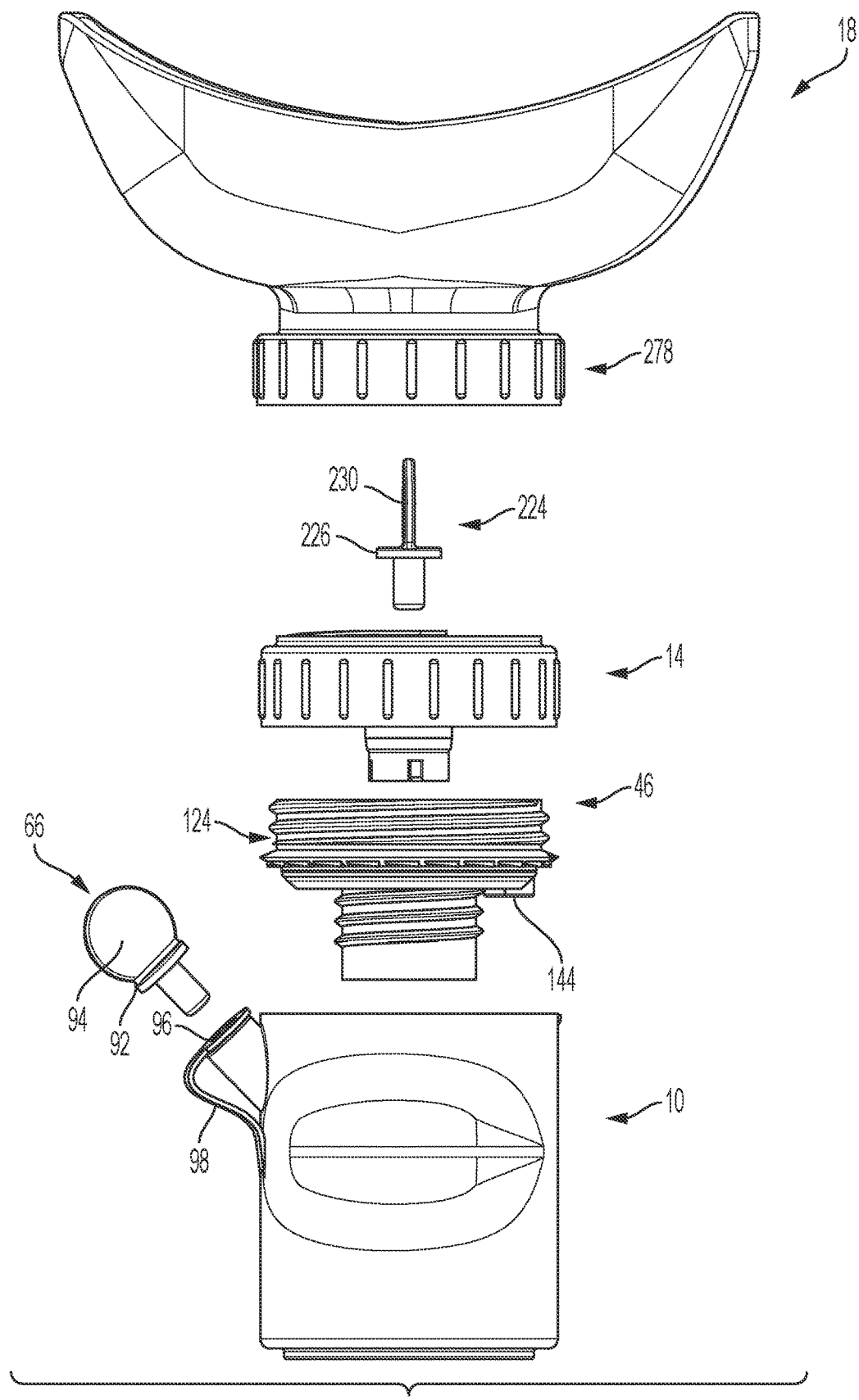
FIG. 13 illustrates a side exploded view of a urine collection assembly according to another embodiment and including a container, a lid and a saddle.
Figure 14:
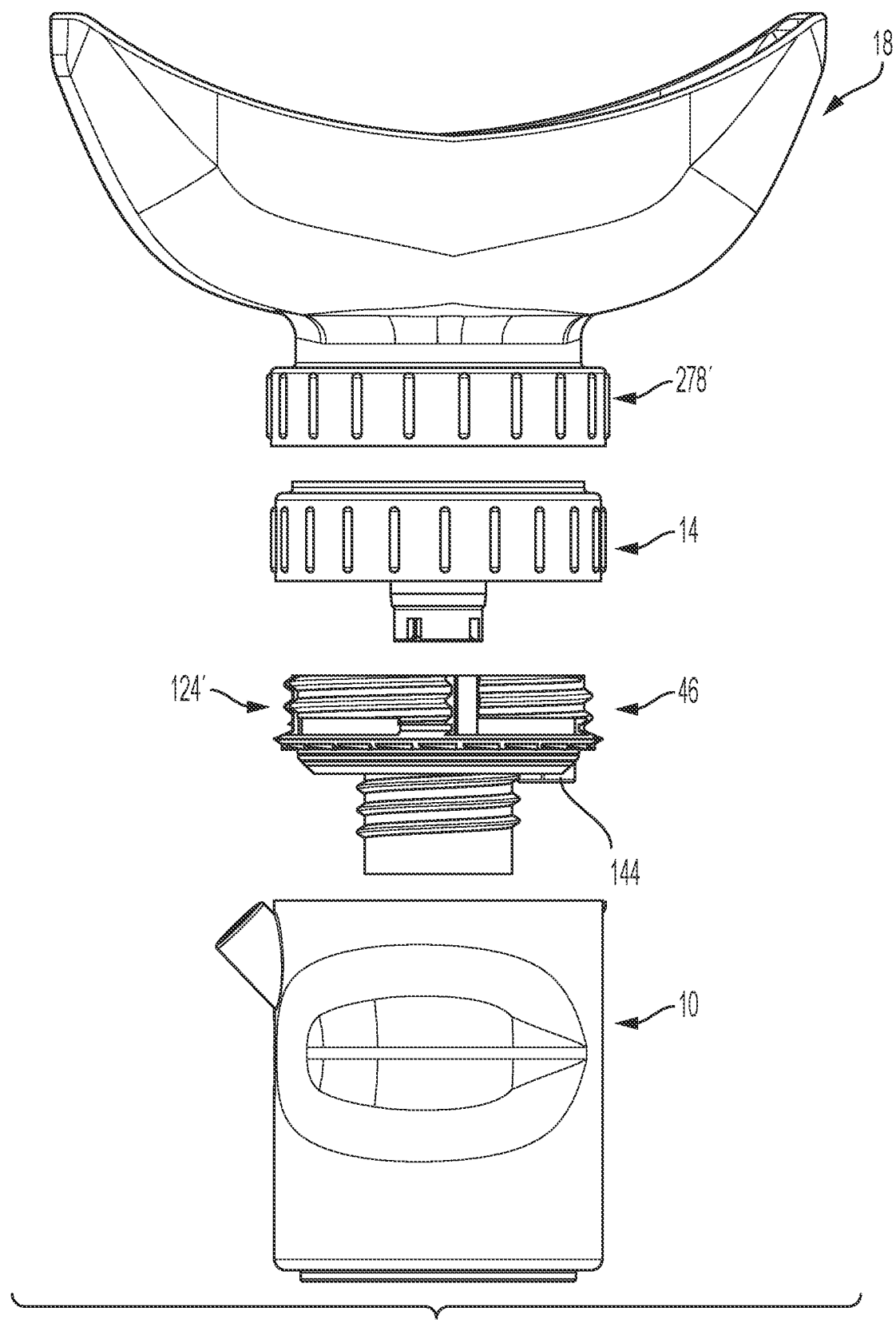
FIG. 14 illustrates a side exploded view of a urine collection assembly according to another embodiment and including a container, a lid and a saddle.
Figure 15:
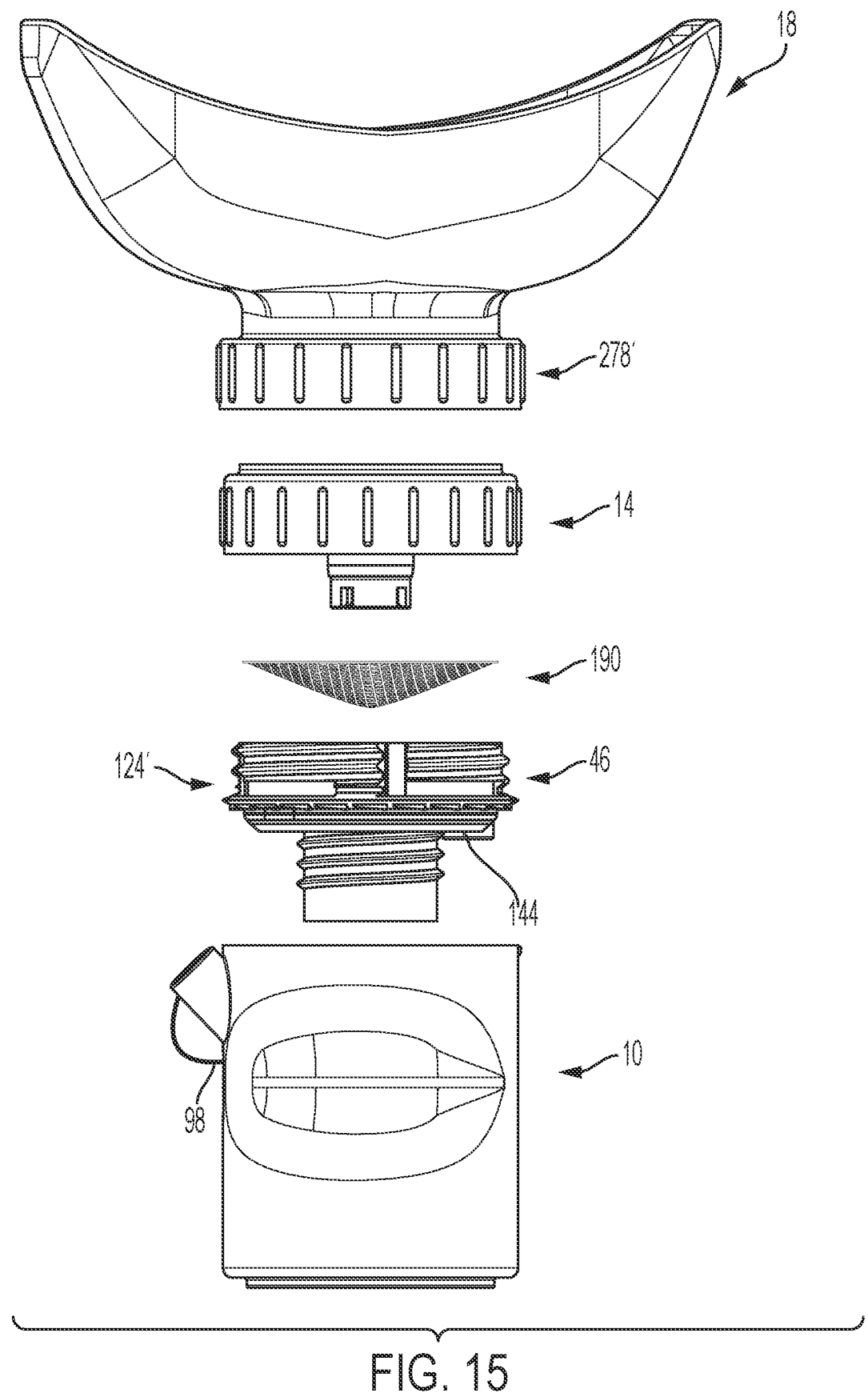
FIG. 15 illustrates a side exploded view of a urine collection assembly according to another embodiment and including a container, a filter, a lid and a saddle.
Figure 16:
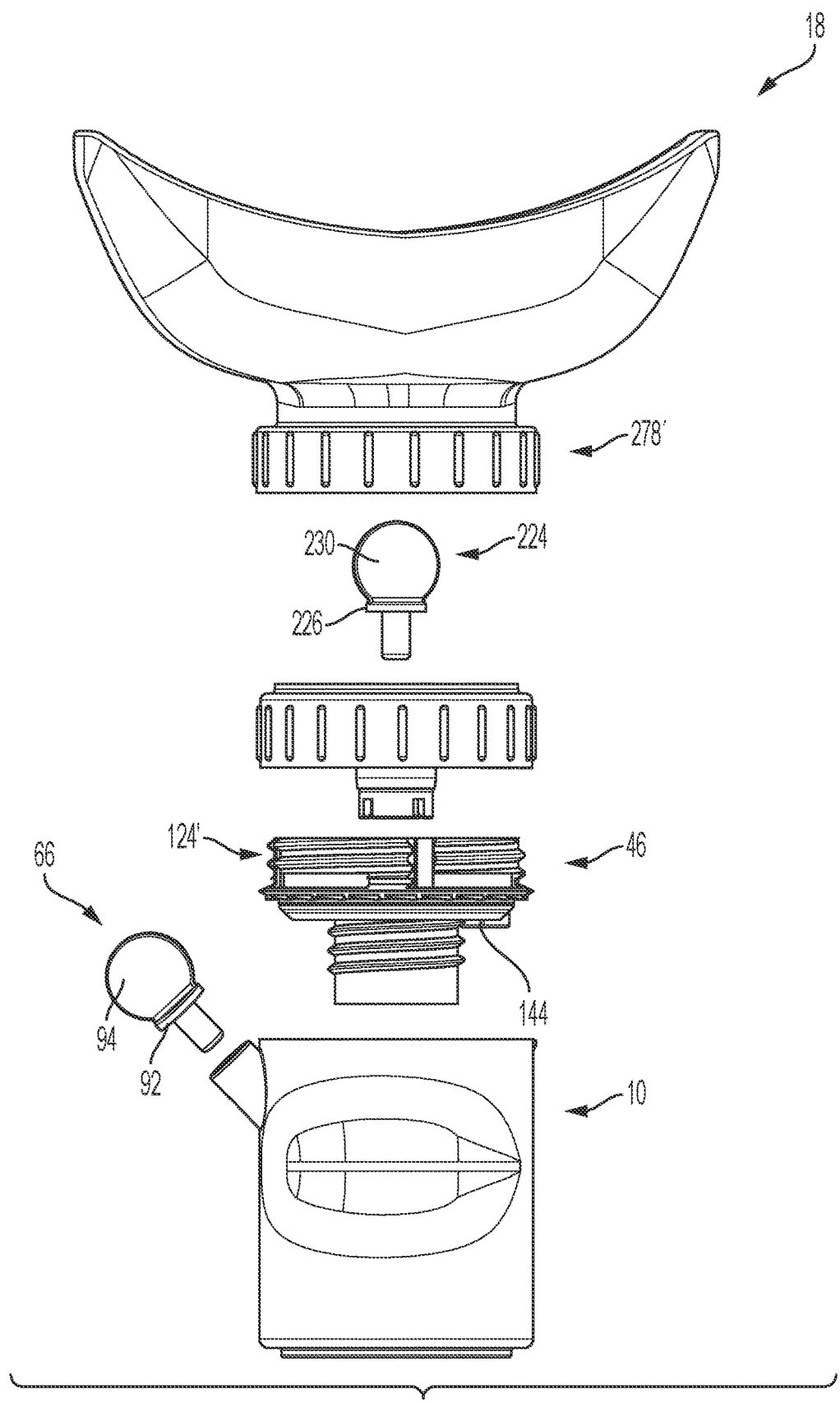
FIG. 16 illustrates a side exploded view of a urine collection assembly according to another embodiment and including a container, a lid and a saddle.

A second inner wall 70 is integrally formed with (or otherwise coupled to) the base 30 and the inner surface 54 of the outer wall 38 and extends from the base 30 toward the second end 26. The second inner wall 70 is positioned on an opposite side of the body 20 relative to the location of the aperture 62. The second inner wall 70 defines a tube or channel 74 that extends parallel to the longitudinal axis A. The tube 74 defines a first opening 78 in the base 30 and a second opening 82 adjacent to the second end 26. In some embodiments (FIGS. 3-6B), the second inner wall 70 at the second opening 82 is positioned at an angle relative to the longitudinal axis A. In the embodiment illustrated in FIGS. 3-6B, the second inner wall 70 at the second opening 82 is positioned at a 45 degree angle relative to the longitudinal axis A, but in other or alternative embodiments second inner wall 70 at the second opening 82 may be positioned at angles ranging from −330 degrees to 30 degrees relative to the longitudinal axis A. In some embodiments (FIGS. 10A-10D), the second inner wall 70 at the second opening 82 is positioned at a substantially perpendicular angle relative to the longitudinal axis A. The term substantially as used herein means plus or minus five degrees. Further, in some embodiments (as shown in FIG. 10B), a tab or protrusion 91 may be positioned adjacent the second opening 82 of the tube 74. In the illustrated embodiments, the tab 91 may extend from the second wall 70 that at least partially defines the tube 74. In other embodiments, the tab 91 may extend from either an outer surface 42b (FIG. 3) of the inner wall 42 or the inner surface 54 (FIG. 3) of the outer wall 38. The outer surface 58 of the outer wall 38 defines a first recess 86 and a second recess 90.

In some embodiments, such as FIG. 1-8, the plug 66 has an elongated body constructed of silicon or rubber and a flange 92 extending about the elongated body on one side thereof. In these embodiments, the flange 92 also serves as a gripping surface. In some embodiments, such as FIGS. 10A, 12, 13, 16, the plug 66 has an elongated body constructed of the same material from which the body 20 (e.g., plastic) is constructed and a flange 92 that extends about the elongated body between opposite sides thereof. Moreover, in the embodiments of FIGS. 10A, 12, 13, 15, one end of the elongated body has a gripping surface 94 projecting from the flange 92. In some embodiments, the plug 66 is manufactured with the body 20 of the container 10, but not directly coupled thereto. In some embodiments (e.g., FIGS. 1-8, 10A, and 13), a retaining clip 96 is integrally formed with or otherwise coupled to the body 20 by a linkage 98. In some embodiments, the retaining clip 96 and the linkage 98 are coupled to and manufactured with body 20 of the container 10, and the retaining clip 96 supports (e.g., receives a portion of) the plug 66. In some embodiments, the retaining clip 96 supports (e.g., may be integrally formed with or otherwise coupled to) the plug 66 such that the plug 66, the retaining clip 96, and the linkage 98 are coupled to and manufactured with the body 20 of the container 10. The retaining clip 96, and therefore the plug 66, may therefore be movable relative to the container 10 via the linkage 98. In any of the embodiments, the plug 66 is removably received and secured (e.g., by a snap fit or friction fit, etc.) in the aperture 62 to selectively close and open the aperture 62. In any of the embodiments, when the plug 66 is received and secured in the aperture 62, the flange 92 helps seal the aperture 62 such that it is airtight, watertight (e.g., fluid), or both airtight and watertight.

With renewed reference to FIGS. 3-6B, the closure element 46 includes a first portion 100, a second portion 104, and an intermediate portion 108 extending between the first portion 100 and the second portion 104. The first portion 100 is substantially cylindrical and therefore has a length and a diameter that is substantially constant along the length. The first portion 100 is configured to be coupled to the first inner wall 42 of the container 10. In particular, the first portion 100 has a threaded portion 112 (FIGS. 5 and 6A) on a portion of a surface thereof that are configured to mate with the threaded portion 50 of the first inner wall 42. An aperture 116 extends from the first portion 100 through the second portion 104 and defines an axis B. The second portion 104 has a first or concave surface 120 that has a diameter that decreases in a direction toward the first portion 100. Accordingly, the first surface 120 of the second portion 104 defines a funnel. The second portion 104 also includes a coupling mechanism 124, 124' on an outer surface. A lip or flange 128 extends circumferentially from the second portion 104 and locking elements 132 are positioned circumferentially about the closure element 46 adjacent the flange 128. The closure element 46 also has a circumferential sealing or valve element 136 that is extends from (or is otherwise coupled to) the second portion 104. In the illustrated embodiment, the sealing element 136 extends at an angle that is substantially the same as the angle of the second opening 82 of the tube 74. The intermediate portion 108 defines a channel 140 extending therethrough. The channel 140 is in fluid communication with the funnel of the second portion 104. In some embodiments, the closure element 46 may further includes a projection 144 extending from the 104. As shown in FIGS. 10A, 10C, and 11-15, the projection 144 extends parallel to the axis B. The projection 144 is configured to selectively engage the tab 91 of the container 10.

In the embodiments shown in FIGS. 3-6 and 11-13, the coupling mechanism 124 of the second portion 104 includes a threaded portion that has threads 124a extending from the outer surface of the second portion 104. In the embodiments shown in FIGS. 3-6 and 11-13, the threaded portion 124 is configured to removably secure the saddle 18 and the cap 14, as will be discussed in detail below.

In the embodiments shown in FIGS. 10A-10C and 14-16, the coupling mechanism 124' includes a threaded portion that has threads 124a'. The coupling mechanism 124' further includes vertical channels 124b' and horizontal channels 124c'. Each of the vertical channels 124b' are in communication with (e.g., connected to or positioned adjacent to) one of the horizontal channels 124c'. As shown, each of the vertical channels 124b' extends through the threads 124a' of the threaded portion and substantially along the height of the second portion 104 of the closure element 46. Each of the horizontal channels 124c' has an open end positioned adjacent the respect vertical channel 124b and a closed end opposite the open end. Each of the horizontal channels 124c' extends from the respective vertical channel 124b' about the circumference of the second portion 104 of the closure element 46. The horizontal channels 124c' are positioned adjacent the flange 128. Each of the horizontal channels 124c' defines a radial distance along the circumference of the second portion 104. In the illustrated embodiments, there are four vertical channels 124b' that are spaced at equal intervals relative to each other about the circumference of the second portion 104, and therefore there are four corresponding horizontal channels 124c' that are spaced at equal intervals relative to each other about the circumference of the second portion 104. In other embodiments, there may be more vertical channels 124b', and therefore more or fewer horizontal channels 124c'. The vertical channels 124b' (and therefore the horizontal channels 124c') may be spaced at equal or non-equal intervals in other embodiments. The channels 124b', 124c' do not interfere with the use of the threads 124a' of the threaded portion. In the embodiments shown in FIGS. 10A-10C and 14-15, the threaded portion is configured to removably secure the cap 14 and the channels 124b', 124c' are configured to act as a quick-connect for quickly connecting and positioning the saddle 18 relative to the container 10 prior to use and then quickly disconnecting the saddle 18 after use, as will be discussed in detail below.

The closure element 46 has a first position (FIGS. 4 and 6A-6B) and a second position (FIG. 3). In the first position, the first portion 100 is coupled to the first inner wall 42, the axis B is aligned with the longitudinal axis A, the second portion 104 extends from the body 20, and the flange 128 and sealing element 136 are spaced apart from the second end 26 of the body 20 by a gap 150. Therefore, in the first position the sealing element 136 is spaced apart from the second opening 82 of the tube 74. In the second position, the first portion 100 is coupled to the first inner wall 42, the axis B is aligned with the longitudinal axis A, the second portion 104 extends from the body 20, and the flange 128 and the sealing element 136 abut the second end 26 of the body 20 thereby eliminating the gap 150. Therefore, in the second position the sealing element 136 abuts or closes the second opening 82 of the tube 74. Moreover, in the second position the projection 144 of the closure element 46 engages the tab 91 of the container 10. Accordingly, the projection 144 prevents the backward rotation of the closure element 46 by engagement with the tab 91 of the container 10, as will be discussed below. The locking elements 34, 132 of the body 20 and the closure element 46 are configured to engage one another to create friction therebetween. When coupling the closure element 46 to the body 20 initially, the user couples (e.g., rotates or twists) the closure element 46 to the body 20 until a first friction level is felt as a result of engagement of the locking elements 34, 132. At this point the closure element 146 is in the first position. To move the closure element 46 from the first position to the second position, the user continues to couple (e.g., rotate or twists) the closure element 46 to increase the friction until a second friction level is felt. At this point the closure element 46 is in the second position.

As shown in FIGS. 3, 5, 6A, and 6B, a first collection chamber 160 is defined by the inner wall 42 and a second collection chamber 170 is defined between the inner wall 42 and the outer wall 38. The first collection chamber 160 is configured to receive between 10 ml and 30 ml of fluid. In one construction, the first collection chamber 160 is configured to receive 10 ml to 15 ml of fluid. The second collection chamber 170 is configured to receive between 15 ml and 100 ml of fluid. In one construction, the second collection chamber 170 is configured to receive at least 30 ml of fluid. The first collection 160 chamber includes a one-way valve 180 that allows fluid to enter the first collection chamber 160 via the aperture 46 in the closure element 46. In the illustrated embodiment, the one-way valve 180 is a valve element (e.g., a ball valve) that is positioned within the first collection chamber 160. The valve element 180 is substantially spherical and formed from a material that is less dense than urine. The valve element 180 may also be constructed from a waterproof material. The valve element 180 is movable along the longitudinal axis A between a first position and a second position. In the first position, the valve element 180 is adjacent to (e.g., supported by) the base 30 within the first collection chamber 160. In the second position, the valve element 180 is positioned within the first portion 100 of the closure element 46 and closes or blocks the aperture 116 in the closer element 146, as will be discussed in greater detail below. In some embodiments, a screen or filter 190 (FIG. 15) may be positioned between the funnel and the first collection chamber 160. For example, the filter 190 may be positioned in the aperture 116 of the closure element 46 between the first portion 100 and the second portion 104. The filter 190 may be configured to prevent debris (e.g., kidney or bladder stones, radiation seeds, etc.) from entering the container 10.

As shown in at least FIGS. 1-3 and 11-16, the lid 14 includes a body 200 having a wall 204 that extends from the body 204. The wall 204 encloses a first space 208 that is defined by a first diameter and a second space 212 that is in fluid communication with the first space 208 and is defined by a second diameter that is smaller than the first diameter. The first space 208 and the second space 212 communicate with one another and are aligned along an axis C. The wall 204 has an intermediate angled portion 216 and openings or recesses 218 (only one of which is shown in FIG. 3) positioned adjacent a distal end. An aperture 220 extends through the body 200, is in communication with first space 208, and is aligned along the axis C. The aperture 220 removably receives a plug 224. The lid 14 includes a coupling mechanism 228 that is configured to mate with the coupling mechanism of 124, 124' of the second portion 104 of the container 10. In the illustrated embodiment, the coupling mechanism 228 is a threaded portion that has threads 228a, which are configured to mate with the threads 124a, 124a' of the closure element 46 of the second portion 104 of the container 10. That is, the user rotates the lid 14 relative to the closure 46 of the container 10 to threadably secure lid 14 onto the container 10. More specifically, regardless of the coupling mechanism 124, 124' of the container 10, the threaded portion (e.g., threads 228a) of the coupling mechanism 228 of lid 14 is configured to matingly receive threaded portion (e.g., the threads 124a, 124a') of the coupling mechanism 124, 124' to removably secure the lid 14 to the container 10.

Like the plug 66 that is usable with the container, the plug 224 has similar variations. That is, in some embodiments, such as FIGS. 1-3, the plug 224 has an elongated body constructed of silicon or rubber and a flange 226 extending about the elongated body one side thereof. In some embodiments, such as FIGS. 10A, 12, 13, 16, the plug 224 has an elongated body constructed of the same material from which the lid 14 (e.g., plastic) is constructed and a flange 226 extends about the elongated body between opposite sides thereof. Moreover, in the embodiments of FIGS. 10A, 12, 13, 16, one end of the elongated body has a gripping surface 230 projecting from the flange 226. In some embodiments, the plug 224 is manufactured with body 200 of the lid 14, but not directedly coupled thereto. In some embodiments (FIGS. 1-3), a retaining clip 232 is integrally formed with or other otherwise coupled to the body 200 by a linkage 234. In some embodiments, the retaining clip 232 and the linkage 234 are coupled to and manufactured with body 200 of the lid 14 and the retaining clip 232 supports (e.g., receives a portion of) the plug 224. In some embodiments, the retaining clip 232 supports (e.g., may be integrally formed with or otherwise coupled to) the plug 224 such that the plug 224, the retaining clip 232, and the linkage 234 are coupled to and manufactured with body 200 of the lid 14. The retaining clip 232, and therefore the plug 224, may therefore movable relative to the lid 14 via the linkage 234. In any of the embodiments, the plug 224 is removably received and secured (e.g., by a snap fit or friction fit, etc.) in the aperture 220 to selectively close and open the aperture 220. In any of the embodiments, when the plug 224 is received and secure in the aperture 220 the flange 226 helps seal the aperture 220 such that is airtight, watertight (e.g., fluid) tight, or both airtight and watertight.

With respect to FIGS. 7-8, the saddle 18 includes a body 250 that defines a basin or bowl 254, a wall 256 coupled to and extending from the basin 258, and an aperture 258 extending through the basin 258. The wall 256 and the aperture 258 are concentric with respect to one another. The basin 254 is substantially ovular-shaped when viewed from the top. The basin 254 has a first end 262, a second end 266 that is opposite the first end 262, a first side 270 that extends between the first end 262 and the second end 266, and a second side 274 that extends between the first end 262 and the second end 266. In some embodiments (such as 1-2, 4A-6, 8-10), the saddle 18 is asymmetrical. Accordingly, as shown in FIGS. 7-8, the first end 262 is elevated relative to the second end 266, and the first side 270 and the second side 274 are parallel to one another. The aperture 258 is positioned closer to the second end 266 than the first end 262. That is, a distance from an axis D extending through the aperture to the first end is greater than a distance from the axis D to the second end. In some embodiments (FIGS. 9A-9C, 10A and FIGS. 11-16), the saddle 18 is symmetrical. Accordingly, as shown in FIGS. 9A-9C, 10A and FIGS. 11-16, the first end 262 and the second end 266 are at substantially the same height relative to a surface of the wall 256, and the first side 270 and the second side 274 are parallel to one another. The aperture 258 is positioned centrally relative to the first end 262 and the second end 266. That is, a distance from an axis D extending through the aperture 258 to the first end 262 is substantially the same as a distance from the axis D to the second end 266. Whether the saddle 18 is asymmetrical or symmetrical, the wall 256 further includes a coupling mechanism 278, 278' (e.g., a threaded portion with or without lugs) on an inner surface thereof that is configured to mate with the coupling mechanism 124, 124' of the closure element 46 of the container 10.

In the embodiments shown in FIGS. 1-8 and 11-13, the coupling mechanism 278 of the wall includes a threaded portion that has threads 278a extending from the inner surface of the wall 256. That is, the user rotates the saddle 18 relative to the closure 46 of the container 10 to threadably secure saddle 18 onto the container 10. More specifically, the threaded portion (e.g., the threads 278a) of the coupling mechanism 278 of FIGS. 1-8 and 11-13 is configured to matingly receive the threaded portion (e.g., the threads 124a) of the coupling mechanism 124 of FIGS. 1-8 and 11-13 to secure the removably secure the saddle 18 to the container 10.

In the embodiments shown in FIGS. 10A, 10D, and 14-16, the coupling mechanism 278' includes a threaded portion that has threads 278a' integrally formed with (or otherwise coupled to) and extending from the inner surface of the wall 256. The coupling mechanism 278' further includes lugs or projections 278b' integrally formed with (or otherwise coupled to) and extending from the inner surface of the wall 256. As shown, the lugs 278b' are positioned at or adjacent to an end of the wall 256, which is opposite the basin 254. In the illustrated embodiments, there are four lugs 278b' that are spaced at equal intervals relative to each other about the circumference of the inner surface of the wall 256. Each of the lugs 278b' corresponds to one of the vertical channels 124b' of the coupling mechanism 124a on the closure element 46, as will be discussed in greater detail below. In other embodiments, there may be more or fewer lugs 278b', there may be a different number of lugs 287b than vertical channels 124b', and they may be spaced at equal or non-equal intervals in other embodiments. The lugs 278b' do not interfere with the use of the threads 278a of the threaded portion.

As noted above, the coupling mechanism 124' of the container 10, together with the coupling mechanism 278' of the saddle 18 are configured to act as a quick-connect for quickly connecting and positioning the saddle 18 of FIGS. 10A, 10D, and 14-16 relative to the container 10 prior to use and then quickly disconnecting the saddle 18 after use. In the embodiments shown in FIGS. 10A, 10D, and 14-16, to couple the saddle 18 to the container 10, the saddle 18 is vertically inserted onto the closure element 46 and twisted (e.g., rotated, pivoted) about the axes A, B. More specifically, the user aligns each of the lugs 278b' with one of the vertical channels 126b'. The user then moves the lugs 278b' vertically within the respective vertical channel 126b' until the lugs 278b' reach the respective the horizontal channel 124c'. Then the user twists (e.g., rotates, pivots) the saddle 18 relative to the closure element 46 of the container 10 until the lugs 278b' are positioned adjacent the closed end of the respective horizontal channel 124c'. To remove the saddle 18, the operation above is reversed.

As noted throughout the preceding paragraphs, FIGS. 1-16 illustrate embodiments of the urine collection assembly having various combinations of the features described above. Although only shown with respect to the symmetrical design of the saddle 18, it should be understood that the asymmetrical design of the saddle 18 may include the coupling mechanism 278' in lieu of the coupling mechanism 278'. The urine collection assembly may include any of the features described herein for the container 10, lid 14, and saddle 18 in any combination.

Figure 17C:
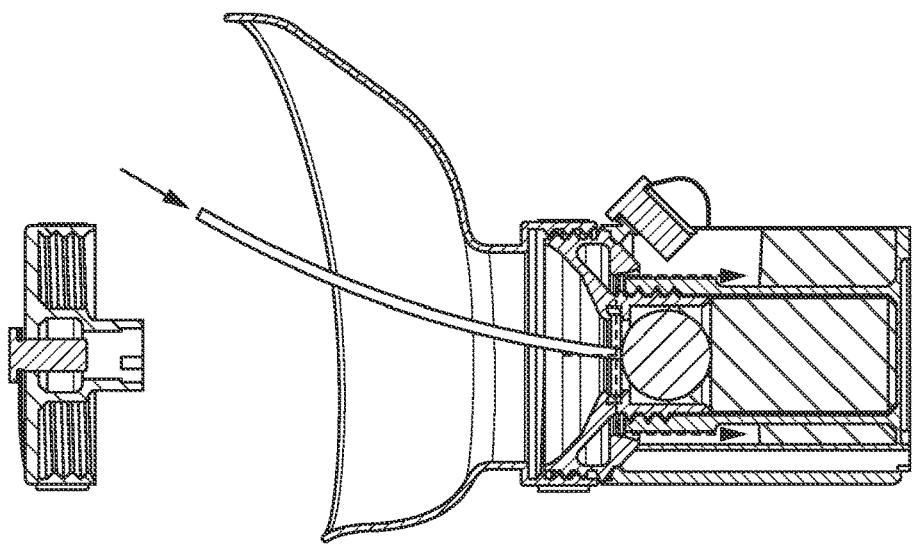
FIG. 17C illustrates a side view of a third step in the process of collecting a urine sample using the urine collection assembly illustrated in the embodiments of FIGS. 7, 10A, and 11-16.
Figure 17B:
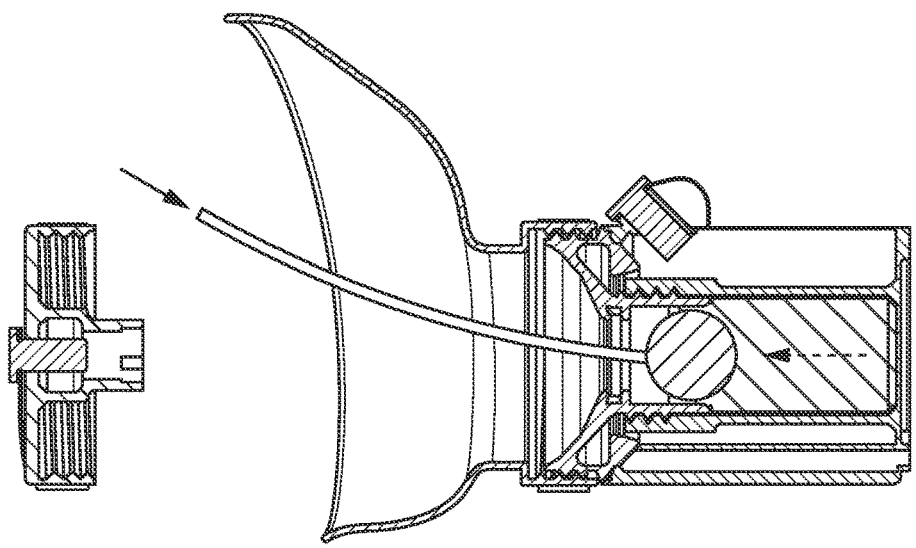
FIG. 17B illustrates a side view of a second step in the process of collecting a urine sample using the urine collection assembly illustrated in the embodiments of FIGS. 7, 10A, and 11-16.
Figure 17A:
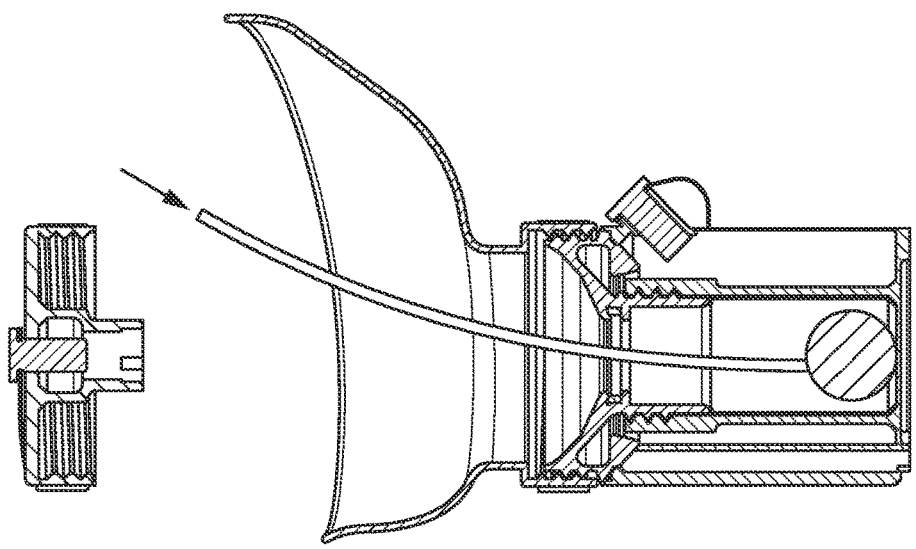
FIG. 17A illustrates a side view of a first step in a process of collecting a urine sample using the urine collection assembly illustrated in the embodiments of FIGS. 7, 10A, and 11-16.

With respect to FIGS. 17A-20B, to use the urine collection assembly, a user or technician may first assemble the container 10 by connecting the closure element 46 to the body 20 such that the closure element 46 is in the first position, as discussed above. Then, the user or technician assembles a urine collection container using the saddle 18 and the container 10. In particular, the user couples the saddle 18 to the container 10 (via either the threaded coupling mechanism 124, 278 or quick-connect coupling mechanisms 124', 278') such that the axis D of the aperture 258 of the saddle 18 aligns with the longitudinal axis A of the container 10. If the asymmetrical saddle 18 is used it is preferred that the first end 262 of the basin 254 is positioned on the side of the container 10 having the aperture 62 and the second end 266 of the basin 254 is positioned on the side of the container 10 having the tube 74. If the symmetrical saddle 18 is used there is little preference as to which of the first end 262 or second end 266 of the basin 254 is positioned on the side of the container 10 having the aperture 62 and which of the first end 262 or second end 266 of the basin 254 is positioned on the side of the container 10 having the tube 74. In some embodiments, the closure element 46 may be pre-assembled with the container 10 and the container 10 may be pre-assembled assembly with the saddle 18. Prior to use, the valve element 180 will be in the first position (FIGS. 17A, 18A). For either a right-handed or a left handed person, the user may then positions one or more fingers in the first recess 86 and one or more fingers in the second recess 90 with their palm facing in any suitable direction (e.g., toward the aperture 62 or generally downwardly).

Figure 17E:
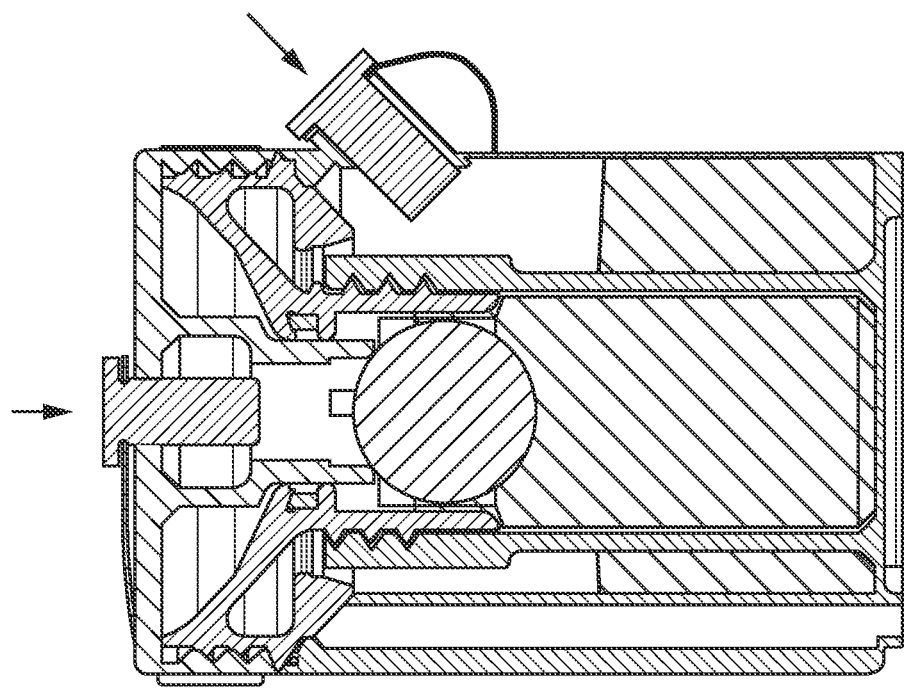
FIG. 17E illustrates a side view of a fifth step in the process of collecting a urine sample using the urine collection assembly illustrated in the embodiments of FIGS. 7, 10A, and 11-16.
Figure 17D:
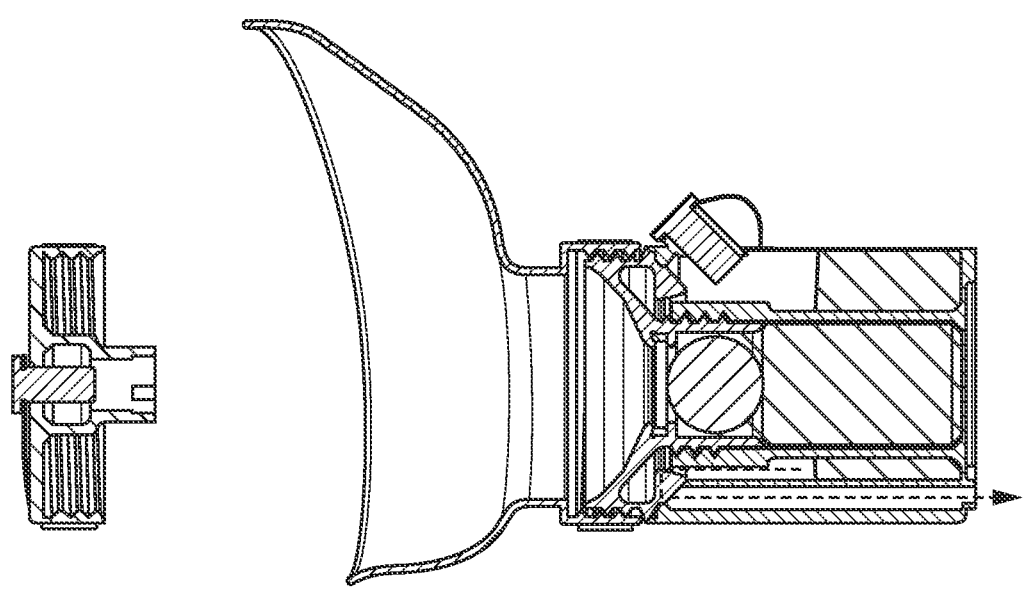
FIG. 17D illustrates a side view of a fourth step in the process of collecting a urine sample using the urine collection assembly illustrated in the embodiments of FIGS. 7, 10A, and 11-16.
Figure 18A:
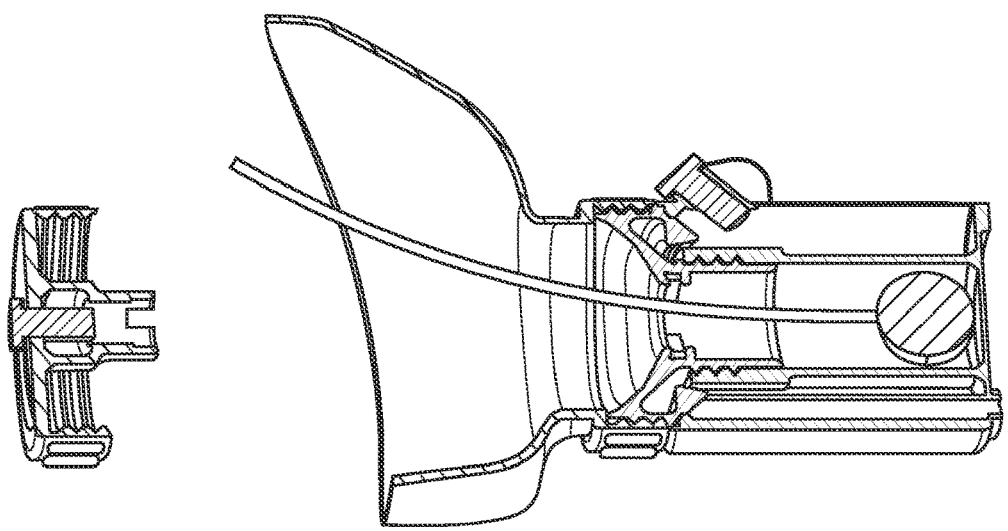
FIG. 18A illustrates a perspective view of the first step in the process of collecting a urine sample using the urine collection assembly illustrated in the embodiments of FIGS. 7, 10A, and 11-16.
Figure 18B:
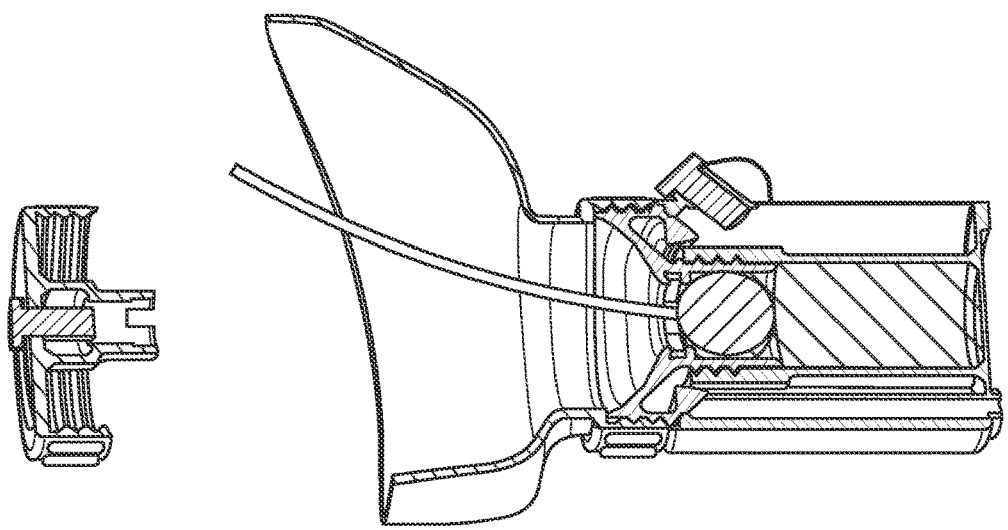
FIG. 18B illustrates a perspective view of the second step in the process of collecting a urine sample using the urine collection assembly illustrated in the embodiments of FIGS. 7, 10A, and 11-16.
Figure 18C:
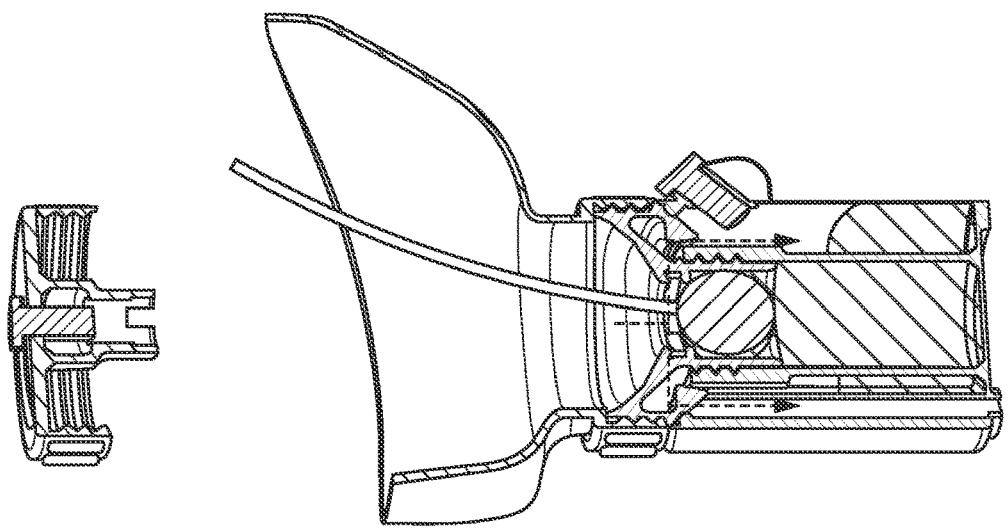
FIG. 18C illustrates a perspective view of the third step in the process of collecting a urine sample using the urine collection assembly illustrated in the embodiments of FIGS. 7, 10A, and 11-16.
Figure 18E:
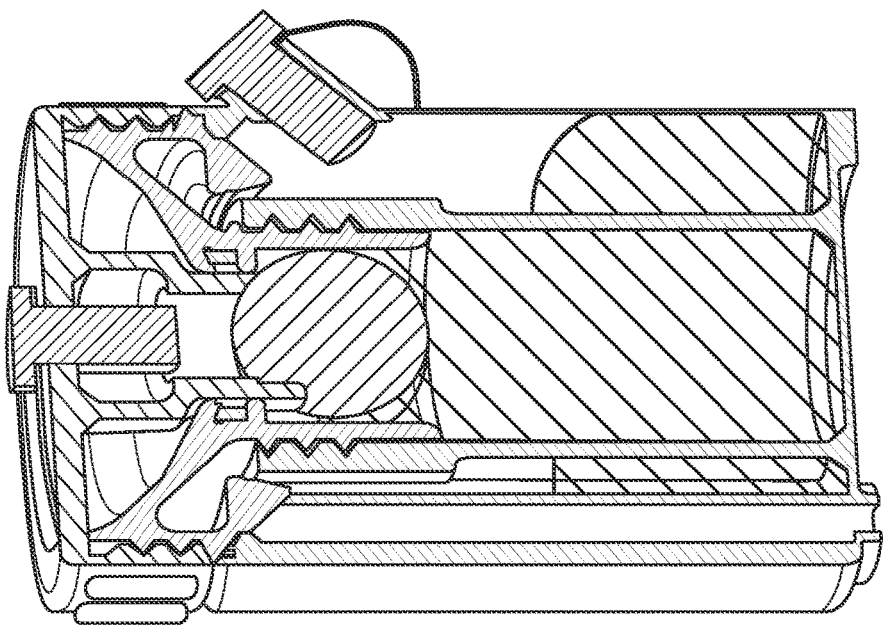
FIG. 18E illustrates a perspective view of the fifth step in the process of collecting a urine sample using the urine collection assembly illustrated in the embodiments of FIGS. 7, 10A, and 11-16.
Figure 18D:
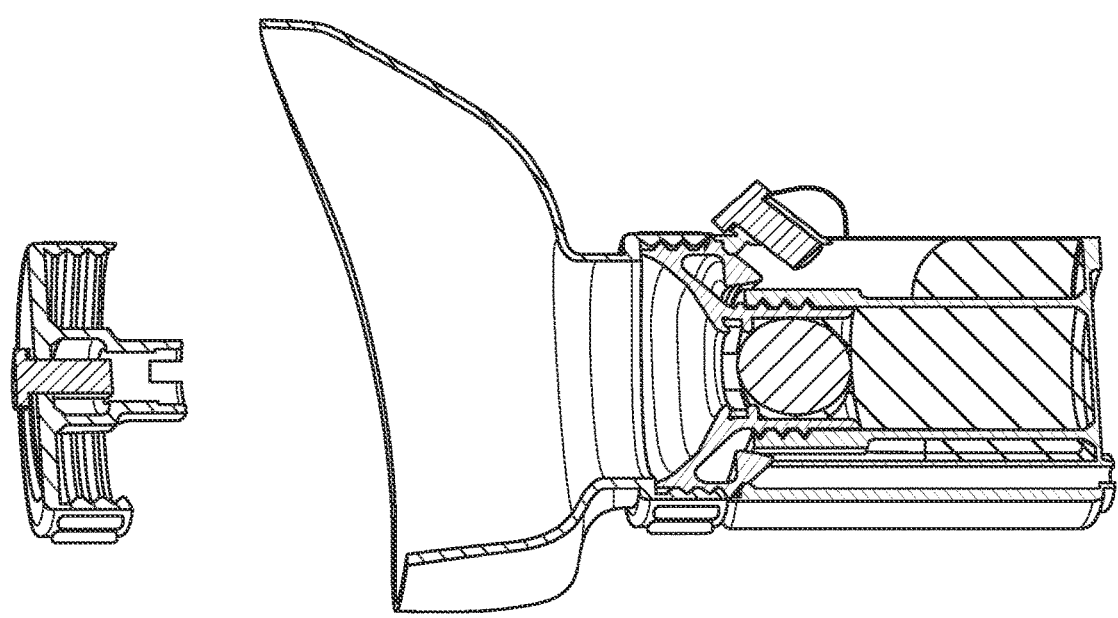
FIG. 18D illustrates a perspective view of the fourth step in the process of collecting a urine sample using the urine collection assembly illustrated in the embodiments of FIGS. 7, 10A, and 11-16.

The user then positions the urine collection container to catch a stream of urine and urinates into the basin 254 of the saddle 18. The saddle 18 is optional. Therefore, when the saddle 18 is not used, the user positions the urine collection container to catch a stream of urine into the first portion 104 of the closure element 46. The recesses 86, 90 provide an ergonomic grip for the body 20 of the container 10 during use. The urine moves from the basin 254 through the aperture 116 in the closure element 46, into the first collection chamber 160 (FIGS. 17B, 18B). As the urine collects in the first collection chamber 160, the valve element 180 will move from the first position to the second position. Urine therefore fills the first collection chamber 160 to collect a first amount of urine (e.g., the first catch). Once the first collection chamber 160 is closed, urine is forced to move from the basin 254 through the channel 140 into the second collection chamber 170 (FIGS. 17C, 18C). Urine will continue to fill the second collection chamber 170 until the user is done urinating. This is because excess urine will enter the second opening 82 of the tube 74 and be expelled into the toilet through the first opening 78 in the tube 74, which extends through base of the container 10 (FIGS. 17D, 18D). The second collection chamber 170 therefore collects a "mid-stream clean catch (MSCC)." Accordingly, the first catch of urine is automatically separated from the MSCC, rather than manually by the user in a separate step. Notably, the first catch of urine is automatically separated from the MSCC without visual indicators.

Once done urinating, the user or technician removes the saddle 18 and assembles the urine storage and testing container. That is, the user or technician then couples the lid 14 to the container 10 (FIGS. 17E, 18E). To couple the lid 14 to the container 10 the user or technician inserts the wall 204 through the aperture 116 in the closure element 46 and couples (e.g., rotates or twists) the lid 14 to threadingly couple the lid 14 to the container 10 (via the coupling mechanism 228 of the lid with the coupling mechanism of the container 124, 124'). When the lid 14 is attached to the container 10, the openings 218 of the wall 204 provide head space for fluid displacement as the valve element 180 is pushed down by the wall 204. As the user or technician couples the lid 14 to the container 10, the closure element 46 will move from the first position to the second position to close the second opening 82 of the tube 74. Additionally and simultaneously, the wall of the lid 14 seals the channel 140 in the closure element 46 to ensure that fluid cannot move between the first and second collection chambers 160, 170 and positions the angled portion 216 of the wall 204 against the funnel 120 of the closure element 46. Moreover, as the user or technician couples the lid 14 to the container 10, the projection 144 of the closure element 46 is advanced beyond the tab 91 such that the projection 144 engages the tab 91. The engagement of the projection 144 with the tab 91 prevents the backward rotation of the closure element 46 when the lid 14 is fully screwed on thereby preventing counter rotation. The engagement of the projection 144 with the tab 91 therefore prevents the tube 74 from accidently opening due to the counter rotation of the closure element 46 and prevents accidental leakage of the contents of the second collection chamber 170. The engagement of the projection 144 with the tab 91 also allows for removal of the lid 14 without unscrewing the closure element 46. As discussed above, the first and second collection chambers 160, 170 are closed by the respective plugs 66, 224.

The urine storage and testing container is transportable. Additionally, and with respect to FIGS. 19A-20B, the plug 224 in the aperture 220 in the lid 14 is removable such that a technician can insert a pipette therethrough and collect a portion of first catch urine sample from the first collection chamber 160 and the plug 66 in the aperture 62 in the outer wall 38 is removable such that a technician can insert a pipette therethrough and collect a portion of the MSCC urine sample from the second collection chamber 170. When the pipette is inserted into the first collection chamber 160 of the container 10, the openings 218 of the wall 204 provide head space for fluid displacement as the valve element 180 is pushed down by the pipette. Depending on the test ordered by the physician, the first catch can either be disregarded or used for nucleic acid amplification tests (NAAT), which are used to identify STIs and STDs such as chlamydia, gonorrhea, gonococci, beta-haemolytic streptococci, Staphylococcus Aureus, candida, among others. Moreover, the MSCC can be used for culture and sensitivity testing of potential bacterial infections occurring in the urinary tract (bladder, kidneys, etc.). Accordingly, the technician can easily collect a sample from one or both of the first and second collection chambers depending on the tests ordered by the physician.

The urine collection assembly may be manufactured using a type of medical grade plastic. For example, the elements of the urine collection assembly may be formed from one or more of the following materials: polypropylene (PP), by polyethylene terephthalate (PET, PETE), high density polyethylene (HDPE), low density polyethylene (LDPE) and/or polyvinyl chloride (PVC, Vinyl). At least some of these materials are appropriate for various forms of sterilization as urine collection assembly may be sterilized at some point prior to use by the patient. The list of materials above is not exhaustive, and therefore elements of the urine collection assembly may be formed from any suitable material.

The urine collection assembly may be manufactured by assembling multiple parts, which may be formed by blow molding, injection molding, extrusion blow molding, injection blow molding, injection stretch blow molding, die forming, molding, thermoforming, or vacuum forming. Other forms of manufacturing may include: 3D printing, extrusion, and UV 3D resin printing/manufacturing. The manufactured parts may be assembled into the proper configuration for use using, for example, sonic welding or any other suitable coupling method.

Sterilization may occur during manufacturing or at the pre-packaging stage. Sterilization may occur by chemical sterilization (e.g., with one or more of nitrogen dioxide (NO2), ethylene oxide (EO), utilizing hydrogen peroxide, and peracetic acid). Alternatively, sterilization may also be accomplished by radiation sterilization (e.g., gamma radiation, electron beam processing, high-energy X-rays, or other forms of irradiation), autoclaving, steam sterilization, dry heat sterilization, or any other FDA approved sterilization method.

The parts of the urine collection assembly that will likely be in contact with the urine specimen may be coated with a hydrophobic coating or compound. The hydrophobic coating may help to ensure that a majority of the first catch will pass through closure element 46 and into the first collection chamber 160. In this way, the first collection chamber 160 will capture the cellular debris and other biological material that is important to properly performing a NAAT test on the first catch but that would otherwise be viewed as a contaminant to the MSCC portion of the sample. In other or additional embodiments, the materials of the urine collection assembly may be sufficiently hydrophobic on their own and not require a separate application of a hydrophobic coating.

The benefits of the urine collection container include its capability of automatically collecting and separating a "first catch" and a "mid-stream clean-catch" sample from a patient, minimizing the cognitive load and physical requirements placed on the patient thereby reducing the chances for error or contamination, and improving patient compliance and patient satisfaction. Moreover, the urine collection assembly enables improvements in the collection process to provide better or more high-quality samples for testing. Providing better samples and separate samples (e.g., samples from the first catch and the mid-stream clean-catch) for testing will provide for improved results in the form of more accurate diagnosis and prescribed course of treatment.

Current methods require considerable cognitive and physical demands on the patient providing the sample. This innovative device is designed to automatically collect and separate both a first catch and a MSCC sample with minimal cognitive and physical demands on the patient. The new innovation simply requires the patient to urinate directly into the device at the start of the sample collection process. This removes several steps of the conventional MSCC method, such as utilizing a towelette or other type of sanitary wipe to clean the opening of the urethra, voiding or collecting the first catch, and approximating the correct amount of urine retained in the cup. More specifically, the container 10 allows for the automatic collection of an initial (first-catch) void sample without the need for a separate sample cup or any additional steps on the part of the user. Additionally, the container 10 protects against the possibility of overfilling container 10 and having urine spill out onto the user. It also allows for ease of sample extraction by a technician through the use of the apertures 62, 220 provided.

Various features and advantages of the invention are set forth in the following claims.

What is claimed is:

1. A urine collection assembly comprising:
   a container including a first collection chamber and a second collection chamber;
   a funnel removably coupled to the container, the funnel in selective fluid communication with the first collection chamber and the second collection chamber;
   a valve positioned within the first collection chamber and movable between a first position and a second position; and a lid removably coupleable to the funnel,
wherein when the valve is in the first position, the first collection chamber is in fluid communication with the funnel to collect a first catch of urine, and
wherein when the valve is in the second position, fluid communication between the first collection chamber and the funnel is prevented, and wherein the second collection chamber is in fluid communication with the funnel to collect a second catch of the urine,
wherein the container further includes a channel that is in fluid communication with the second collection chamber, the channel having a first opening adjacent a first end of the container and a second opening adjacent a second end of the container, the channel being configured to guide an excess amount of the urine from the second collection chamber to a location outside of the container, and
wherein the funnel includes a sealing element and is movable between a third position in which a gap exists between the container and the sealing element and a fourth position in which no gap exists between the sealing element and the container, the sealing element configured to prevent fluid communication between the second collection chamber and the channel when the funnel is in the fourth position.

2. The urine collection assembly of claim 1, wherein the valve is spaced apart from the funnel in the first position, and wherein the valve is configured to close an aperture in the funnel in the second position.

3. The urine collection assembly of claim 1, wherein the funnel is configured to move from the third position to the fourth position when the lid is coupled to the container.

4. The urine collection assembly of claim 1, wherein the funnel includes a projection extending therefrom, the projection selectively engageable with a tab on the container to prevent counter rotation of the funnel with respect to the container when the funnel is in the fourth position.

5. The urine collection assembly of claim 1, further comprising a saddle removably coupleable to the funnel, the saddle configured to guide the urine into the container.

6. The urine collection assembly of claim 1, further comprising a filter for separating debris from the urine that enters the container, the filter positioned between the funnel and the first collection chamber.

7. A urine collection assembly comprising:
a container including a first collection chamber and a second collection chamber;
a funnel removably coupled to the container, the funnel in selective fluid communication with the first collection chamber and the second collection chamber;
a ball valve within the first collection chamber, the ball valve configured to allow fluid communication between the first collection chamber and the funnel to collect a first catch of urine when the ball valve is in a first position, and the ball valve configured to allow fluid communication between the second collection chamber and the funnel to collect a second catch of the urine when the ball valve is in a second position;
a lid removably coupleable to the funnel,
wherein the ball valve is spaced apart from the funnel within the first collection chamber when the ball valve is in the first position, and wherein the ball valve is configured to close an aperture in the funnel when the ball valve is in the second position,
wherein the container further includes a channel in fluid communication with the second collection chamber, the channel having a first opening adjacent a first end of the container and a second opening adjacent a second end of the container, the channel being configured to guide an excess amount of the urine from the second collection chamber to a location outside of the container,
wherein the funnel includes a sealing element and is movable between a third position in which a gap exists between the container and the sealing element and a fourth position in which no gap exists between the sealing element and the container, the sealing member configured to prevent fluid communication between the second collection chamber and the channel when the funnel is in the fourth position, wherein the funnel is configured to move from the third position to the fourth position when the lid is coupled to the container, and
wherein the lid includes a first aperture in fluid communication with the first collection chamber when the lid is coupled to the container and wherein the container further includes a second aperture in fluid communication with the second collection chamber, the first aperture in the lid configured to receive a pipette for collecting a portion of a sample of the urine contained in the first collection chamber and the second aperture in the container configured to receive a pipette for collecting a portion of a sample of the urine contained in the second collection chamber, the first aperture and the second aperture each being selectively closed by a plug.

8. The urine collection assembly of claim 7, further comprising a saddle removably coupleable to the funnel, the saddle configured to guide the urine into the container.

9. The urine collection assembly of claim 8, wherein one or more of the funnel, the first collection chamber, the valve, and the saddle include a hydrophobic coating.

10. The urine collection assembly of claim 7, further comprising a filter for separating debris from the urine that enters the container, the filter positioned between the funnel and the first collection chamber.

11. The urine collection assembly of claim 7, wherein the funnel further includes a projection extending therefrom, the projection selectively engageable with a tab on the container to prevent counter rotation of the funnel with respect to the container when the funnel is in the fourth position.

* * * * *